(12) United States Patent
Damaj

(10) Patent No.: US 8,003,137 B2
(45) Date of Patent: Aug. 23, 2011

(54) **EXTRACTS OF *ARISTOLOCHIA PAUCINERVIS POMEL* AND USES THEREOF**

(75) Inventor: Bassam Damaj, San Diego, CA (US)

(73) Assignee: FasTrack Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/151,843

(22) Filed: May 9, 2008

(65) Prior Publication Data

US 2009/0280202 A1 Nov. 12, 2009

(51) Int. Cl.
*A01N 65/00* (2009.01)

(52) U.S. Cl. ...................................................... 424/725

(58) Field of Classification Search .................. None
See application file for complete search history.

(56) References Cited

U.S. PATENT DOCUMENTS

| | | |
|---|---|---|
| 2002/0099086 A1 | 7/2002 | Achenbach et al. |
| 2006/0121138 A1 | 6/2006 | Johri et al. |
| 2006/0147556 A1 | 7/2006 | Brewer |

FOREIGN PATENT DOCUMENTS

WO  WO 00/06182  2/2000

OTHER PUBLICATIONS

Gadhi et al., Journal of Ethnopharmacology, 67, 1999, pp. 87-92.*
Gadhi et al., Journal of Ethnopharmacology, 75, 2001, pp. 203-205.*
Gadhi et al., Journal of Ethnopharmacology, 75, 2001, pp. 207-212.*
Search of Westlaw Database on Sep. 10, 2007; US. Application 2003/0147973.
Kumar et al., Naturally occurring aristolactams, aristolochic acids and dioxoaporphines and their biological activities, Nat. Prod. Rep., 2003, pp. 565-583, vol. 20, Delhi, India.
Kupchan et al., Tumor Inhibitors. I. Aristolochic Acid, the Active Principle of *Aristolochia indica*, Communications to the Editor, May, 1962, pp. 657-662.
Miller et al., Reporting Results of Cancer Treatment, Cancer, 1981, pp. 207-214, vol. 47.
Hinou et al., Cytotoxic and Antimicrobial Principles from the Roots of *Aristolochia longa*, Int. J. Crude Drug Res., 1990, pp. 149-151, vol. 28, No. 2.
Middleton, Jr., et al., The Effects of Plant Flavonoids on Mammalian Cells: Implications for Inflammation, Hart Disease, and Cancer, Pharmacological Reviews, 2000, pp. 673-751, vol. 52, No. 4.
Hinou et al., Abstract, International Journal of Crude Drug Research, 1990, pp. 149-151, vol. 28, No. 2.
Prasad et al., "Metal hyperaccumulation in plants—Biodiversity prospecting for phyforemediation technology"; Electronic Journal of Biotechnology, ol. 6, No. 3, p. 285-321, Dec. 15, 2003.
International Search Report, PCT/US2008/006010, dated Aug. 8, 2008.
Gadhi et al. Antidermatophytic Properties of Extracts from the Leaves of *Aristolochia paucinervis pomel*. Phytotherapy Research. 2001, pp. 79-81, vol. 15.
*Aristolochia paucinervis*, <http://species.wikimedia.org/wiki/Aristolochia_paucinervis> (retrieved Nov. 22, 2010).
*Aristolochia longa paucinervis* <zipcodezoo.com/Plants/A/Aristolochia_longa_paucinervis/> (retrieved Nov. 22, 2010).
Preliminary Report on Patentability, PCT/US2008/006010 dated Nov. 18, 2010.

* cited by examiner

*Primary Examiner* — Michael Meller
(74) *Attorney, Agent, or Firm* — TraskBritt, P.C.

(57) ABSTRACT

Methods of extracting from a part of a variety of the species *Aristolochia paucinervis* pomel, a biologically active extract, are disclosed. Methods of reducing cell growth in a subject and inducing apoptosis in a cell are also disclosed.

7 Claims, 20 Drawing Sheets

EXTRACTS OF *ARISTOLOCHIA PAUCINERVIS POMEL* AND USES THEREOF

TECHNICAL FIELD

Embodiments of the invention relate to the administration and formation of extracts of *Aristolochia paucinervis* pomel.

BACKGROUND

Cancer refers to any one of a large number of diseases characterized by the development of abnormal cells that divide uncontrollably and have the ability to invade and destroy surrounding tissue. Every year nearly 10 million people around the world join the more than 25 million already living with cancer. It is estimated that half the men and one-third of the women in the United States will develop cancer in their lifetimes. It is also estimated that this year about 1.4 million new cases of cancer will be diagnosed and over half a million people will die of the disease. Despite advances in cancer therapy, cancer remains the second leading cause of death in the United States.

Many types of cancer treatments are currently in use, including chemotherapy, radiation, immunotherapy and surgery. Chemotherapy refers to the use of drugs to destroy cancer cells. Whereas normal cells grow and die in a controlled way, cancer cells divide, and therefore multiply, without control, and chemotherapy drugs generally destroy cancer cells by stopping them from dividing. However, healthy cells may also be damaged, especially those that divide quickly. Damage to such normal cells accounts for many of the side effects of chemotherapy drugs. Side effects are different for each chemotherapy drug, and they also differ based on the dosage, the route the drug is given, and how the drug affects each subject. Some patients experience side effects so severe that chemotherapy must be discontinued. For example, certain types of chemotherapy, such as administering of Carmustine, Lomustine, Ara-C, Cyclophosphamide, and Daunorubicin, are associated with the potential for liver toxicity or permanent liver damage.

Members of the *Aristolochia* family of plants have been used in medicinal preparations according to traditional medicine in various countries throughout the world. For example, *Aristolochia paucinervis* pomel has been marketed for use as a dietary supplement in the Kingdom of Morocco for more than 10 years. Chinese medicines meant to affect weight loss, improve the immune system or alleviate gastrointestinal symptoms have been extracted from *Aristolochia paucinervis* pomel.

BRIEF SUMMARY

The invention described herein relates to a method of reducing cell growth in a subject, comprising administering to the subject an effective amount of a plant extract composition comprising an extract of the plant species *Aristolochia paucinervis* pomel.

Embodiments of the invention include a method of killing tumor cells by administering to a subject having at least one tumor an effective amount of a pharmaceutically acceptable composition comprising an effective amount of a substantially purified extract of the plant species *Aristolochia paucinervis* pomel so as to decrease the tumor volume.

Embodiments of the invention include methods of improving the prognosis of a subject having cancer by administering to the subject an effective amount of a composition comprising an extract of the plant species *Aristolochia paucinervis* pomel.

The invention described herein also includes a method of inducing apoptosis in a cell by treating the cell with an effective amount of a plant extract composition comprising an extract of the plant species *Aristolochia paucinervis* pomel. Accordingly, in one aspect, the invention provides the use of an extract from an *Aristolochia* species, preferably *Aristolochia paucinervis* pomel, or one or more compounds isolable therefrom, for the manufacture of a medicament for the treatment of cancer.

Another embodiment of the invention describes a method of making an extract of the plant species *Aristolochia paucinervis* pomel by obtaining a quantity of *Aristolochia paucinervis* pomel plant matter, contacting the plant matter with an extraction medium comprising water at a temperature between about 20° C. and about 40° C., and separating the extraction medium and extracted components therein from the plant matter.

Embodiments of the invention include methods of administering compositions comprising an extract of *Aristolochia paucinervis* pomel to subjects suffering from cancer to improve the condition of such subjects. In particular, extracts from *Aristolochia paucinervis* pomel have been found to reduce the proliferation of cancer cells, especially colon cancer cells. The extracts have been shown to modulate expression of cytokines, increase cytotoxic activity of T cells, increase PMN and PMNC expression, and decrease tumor growth without harming liver function.

BRIEF DESCRIPTION OF THE FIGURES

In FIG. 12A, transcripts are down-regulated by about 0.3 fold, whereas in FIG. 12B, transcripts are down-regulated by 0.3-0.5 fold; In FIG. 13A, transcripts are up-regulated by three fold or more, whereas in FIG. 13B transcripts are up-regulated two to three fold.

DETAILED DESCRIPTION OF THE INVENTION

Figure 1A:
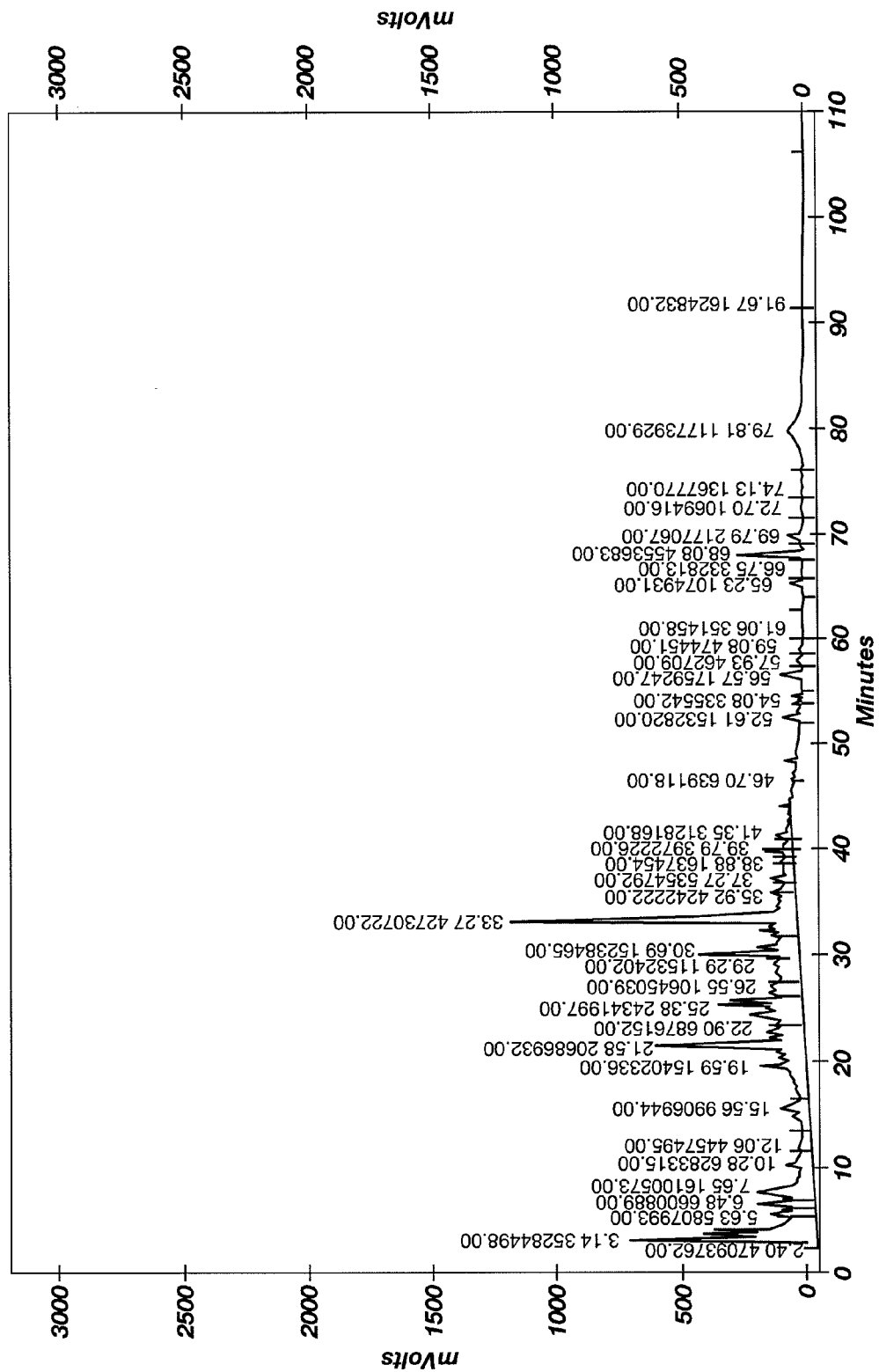
FIG. 1 shows the results of high performance liquid chromatography (HPLC) analysis using a C18 column and detecting at 210 nm of an *A. paucinervis* pomel extract (VRZDN)

Embodiments of the present invention provide plant extract compositions containing an extract of the taxonomic species of plants referred to as *Aristolochia paucinervis* pomel, and methods for using the compositions for reducing unwanted cell growth. Such methods may include in vivo treatment and/or prevention of medical indications that are responsive to cell growth inhibition or killing, as well as in vitro induction of apoptosis. Also provided are methods for making the extracts.

While the present disclosure may be embodied in many different forms, several specific embodiments are discussed herein with the understanding that the present disclosure is to be considered only as an exemplification of the principles of the invention, and it is not intended to limit the invention to the embodiments illustrated.

"Treating" or "treatment" as used herein does not require a complete cure. It means that the symptoms of the underlying disease or condition are at least reduced, and/or that one or more of the underlying cellular, physiological, or biochemical causes or mechanisms causing the symptoms are reduced and/or eliminated. It is understood that reduced, as used in this context, means relative to the state of the disease or condition, including the molecular state of the disease or condition, not just the physiological state of the disease or condition.

Treatment of a disease, disorder, syndrome, condition or symptom refers to those steps that a clinician would take to identify a subject benefiting from such treatment and to administer a composition of the invention to the subject. Treatment thus includes diagnosis of a disease, syndrome, condition, or symptom that is likely to be ameliorated, palliated, improved, eliminated, and/or cured by administering a composition comprising a plant extract of the invention to the subject. Treatment also includes the concomitant amelioration, palliation, improvement, elimination, or cure of the disease, disorder, syndrome, condition, and/or symptom. In some embodiments, treatment implies prevention or delay of onset of a disease, disorder, syndrome, condition or symptom (i.e., prophylaxis), prevention or delay of progression of a disease, disorder, syndrome, condition, or symptom, and/or reduction in severity of a disease, disorder, syndrome, condition or symptom. In the case of neoplastic growth in particular, treatment includes palliation, as well as the reversal, halting or delaying of neoplastic growth. In this regard, treatment may also include remission, including complete and partial remission. In the case of climacteric symptoms, treatment includes prevention and palliation of various symptoms. Compositions comprising an *A. paucinervis* pomel extract may be used to inhibit growth of many types of tumor cells and thus is expected to be useful for treating a variety of types of tumors, including, for example, tumors of colon cancer, non-small cell lung cancers, renal cell carcinomas, central nervous system cancers, leukemias, melanomas, ovarian cancers, breast cancers, and prostate cancers.

As used herein, the term "tumor" represents a single cell or multiple cells. "Tumor" as used herein refers to any growth deregulated cell which may or may not be part of a mass of tissue.

As used herein, the term "growth deregulated cell" represents a single or multiple cancerous cells characterized by unregulated cell growth. A growth deregulated cell may form a mass of tissue that results from excessive cell growth or proliferation, either benign (noncancerous) or malignant (cancerous), including pre-cancerous lesions.

As used herein, the terms "cancer" and "cancerous" refer to or describe the physiological condition in mammals in which a population of cells are characterized by unregulated cell growth. Examples of such may include, but are not limited to, carcinoma, lymphoma, blastoma, sarcoma, and leukemia. More particular examples of such cancers include, but are not limited to, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The phrase, "therapeutically effective" refers to the ability of an active ingredient, for example, *A. paucinervis* pomel extract, to elicit the biological or medical response that is being sought by a researcher, veterinarian, medical doctor or other clinician. Non-limiting examples include, but are not limited to, palliation, reduction of tumor size in a patient, extended survival time, and the like.

The phrase, "therapeutically effective amount" includes the amount of an active ingredient, for example, an extract of *A. paucinervis* pomel, that will elicit the biological or medical response that is being sought by the researcher, veterinarian, medical doctor or other clinician. The compositions of the invention may be administered in amounts effective at palliation, reducing tumor size and/or extending survival time. Alternatively, a therapeutically effective amount of an active ingredient and/or extract is the quantity of the compound required to achieve a desired therapeutic and/or prophylactic effect, such as the amount of the active ingredient and/or extract that results in the prevention of or decrease in the symptoms associated with the condition (for example, to meet an end-point). An effective amount may include an amount with or without undue adverse side effects, including but not limited to, liver toxicity or improvement or elimination of symptoms, and other indicators as are selected as appropriate measures by those skilled in the art.

The terms, "pharmaceutically acceptable" or "pharmacologically acceptable" refer to molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein, the term "extract" means a composition of matter prepared by method comprising contacting an extraction medium with plant material under conditions suitable for drawing one or more chemical compounds from the plant material into the extraction medium, thereby forming an extraction solution. The extraction solution may then separated from the plant material, and may optionally be diluted or reduced, to form the extract. An extract may comprise phyto compounds obtained from plant material of the *Aristolochia paucinervis* pomel plant. An extract may be purified or substantially purified. As used herein "substantially purified" means substantially free of contaminants which are associated with the plant material in its native environment. Purification may be accomplished by either reducing the content of at least one of the components (including impurities) in the unpurified composition as compared to the level before purification or enriching the concentration of one or more components of interest in the composition as compared to the composition before purification.

Plant material means any part or parts of at least one plant from the species *Aristolochia paucinervis* pomel. Plant material may include the whole plant or any part or parts of the plant, such as the bark, root, stem, leaves, flowers, fruit, seeds and/or parts or mixtures of any of the foregoing. Plant material may be fresh cut, dried (including freeze dried), frozen and the like. Plant material may also be whole or separated into small parts. For example, leaves may be chopped, shredded or ground; roots may be chopped or ground; fruit may be chopped, sliced or blended; seeds may be chopped or ground; stems may be shredded, chopped or ground. Thus, a biologically active extract contained in a composition of the invention may be made using various portions of the *Aristolochia paucinervis* pomel plant, such as bark, roots, stems, leaves and combinations thereof. Such extracts are referred to herein as "*A. paucinervis* pomel extracts" or singularly as "*A. paucinervis* pomel extract." The Examples herein describe use of *A. paucinervis* pomel extracts prepared using bark and roots. Similar extracts made from a single portion of the plant may also be useful in the methods described herein. Characterization of an *A. paucinervis* pomel extract is illustrated herein, for example in FIG. 1, which shows results of high performance liquid chromatography (HPLC) analysis using a C18 column and detecting at about 210 nm.

The term "biologically active extract" means an extract from *A. paucinervis* pomel that has biological activities including, but not limited to, palliation, reducing tumor size and/or extending survival time.

Any suitable route of administration may be employed for providing a subject with an effective amount of a composition comprising an extract of *A. paucinervis* pomel. Rectal, parenteral (non-limiting examples include subcutaneous, intramuscular, intravenous), transdermal, topical, oral administration, ocular, otic, nasal administration and like forms of administration are possible. Oral dosage forms include tablets, troches, dispersions, suspensions, solutions, capsules, and the like. A composition of the invention may be administered to a subject by any number of routes known in the art including, by way of non-limiting example, intravenously, intramuscularly, subcutaneously, intraorbitally, intracapsularly, intraperitoneally, intracisternally, intra-articularly, intracerebrally, orally, intravaginally, rectally, topically, intranasally, transdermally or via a nasogastric (ng) tube or other indwelling tubes placed in the GI tract. A specific example of a route for humans is oral administration.

The composition may comprise dry formulations, solutions and/or suspensions of the *A. paucinervis* pomel extracts. As used herein, the terms "suspension" and "solution" are interchangeable with each other and mean solutions and/or suspensions of the *A. paucinervis* pomel extract.

A pharmaceutical composition including an extract of *A. paucinervis* pomel, and derivatives thereof may be used for the treatment of cancer. For example, a pharmaceutical composition comprising an *A. paucinervis* pomel extract may be used for the treatment of ovarian cancer, lymphoma, B lymphocyte myeloma, Hodgkins lymphoma, breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervical cancer. Treatment of these conditions may be accomplished by administering to a subject an effective amount of the pharmaceutical composition according to embodiments of the present invention. In further embodiments, the cancer may be any cancer but leukemia or lung cancer. In yet further embodiments, the cancer may be any cancer but lymphocytic leukemia or bronchial epidermoid carcinoma. In additional embodiments, the cancer may be any cancer but p-388 or NSCLCN6.

A composition of the invention described herein may be formulated and administered by those skilled in the art in a manner and in an amount appropriate for the condition to be treated; the weight, gender, age and health of the subject; the biochemical nature, bioactivity, bioavailability and side effects of the particular compound; and in a manner compatible with concurrent treatment regimens. An appropriate amount and formulation for treating cancer in humans may be extrapolated based on the activity of the compound in the assays and animal models described herein. An appropriate amount and formulation for use in humans for other indications may be extrapolated from other credible animal models known in the art of a specific cancer or proliferative disorder. The effective amount may be chosen to be more or less effective than a particular chemotherapeutic agent. Thus, an amount of the composition suitable for a daily dose may be equivalent to about 0.01 to 100 grams of composition per kilogram body weight of the subject. For example, the daily dose may be about 1 to about 1,000 mg of dry extract per kg body weight. The person skilled in the art may be able to titrate the dose necessary to achieve the desired effect and may likewise recognize that upward or downward deviations from the cited ranges may be tolerated within the scope of the present invention.

The total amount of extract may be administered as a single dose or by infusion over a relatively short period of time, or may be administered in multiple doses administered over a more prolonged period of time. Additionally, the extract may be administered in slow-release matrices, which may be implanted for systemic delivery or at the site of the target tissue. Contemplated matrices useful for controlled release of therapeutic compounds are well known in the art, and include materials such as DEPOFOAM®, biopolymers, micropumps, and the like.

A composition of the invention may be administered in neat form as well as in a composition with one or more other ingredients. For example, an *A. paucinervis* pomel composition of the invention may be administered to a subject as a pharmaceutical composition comprising the extract and a pharmaceutically acceptable carrier. Those skilled in the art understand that the choice of a pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier may contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins. The administered material may exist in any of a variety of formats, including, for example, an aqueous solution, a gel, powder, capsule and tablet. The administered material may contain a suitable carrier, diluent, dispersion media, filler, solid carrier, coating, antifungal agent, antibacterial agent, dermal penetration agent, surfactant, isotonic agent, absorption agent, and the like.

A composition of the invention may be included also in a food composition for administration to the subject. Examples of food materials are brown sugar, rice, wheat, corn, potato, sweet potato, soybean flour, seaweed (sea tangle, wakame (*Undaria pinnatifida*), agar-agar, etc.) flour, starch syrup, lactose, glucose, fructose, sucrose, mannitol, and the like. These materials may be used alone or in suitable combination with one another. The food composition may contain flavoring agents, coloring agents, sweetening agents, edible oils, vitamins, and the like.

For applications that require the compounds and compositions to cross the blood-brain barrier, formulations that increase the lipophilicity of the compounds in the extract are particularly desirable. For example, the extract may be incorporated into liposomes (Gregoriadis, Liposome Technology, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

The terms, "individual," "patient," or "subject" are used interchangeably herein and include any mammal, including animals, for example, primates, for example, humans, and other animals, for example, dogs, cats, swine, cattle, sheep, and horses. The compounds of the invention can be administered to a mammal, such as a human, but may also be administered to other mammals, for example, an animal in need of veterinary treatment, for example, domestic animals (for example, dogs, cats, and the like), farm animals (for example, cows, sheep, pigs, horses, and the like) and laboratory animals (for example, rats, mice, guinea pigs, and the like). As used herein, the term "subject" includes cells in a culture or tumor tissue cells.

In one embodiment, a liquid oral pharmaceutical composition may be prepared by mixing an *A. paucinervis* pomel extract with a solution including a buffering agent. For example, *A. paucinervis* pomel extract, may be mixed with a sodium bicarbonate solution to achieve a desired final *A. paucinervis* pomel concentration.

Although sodium bicarbonate is one buffering agent which is employed in certain embodiments of the invention to protect the *A. paucinervis* pomel extract against acid degradation, many other weak and strong bases (and mixtures thereof) may be utilized. For the purposes of this application, "buffering agent" shall mean any pharmaceutically appropriate weak base or strong base (and mixtures thereof) that, when formulated or delivered with (e.g., before, during and/or after) the *A. paucinervis* pomel extract and functions to substantially prevent or inhibit the acid degradation of the *A. paucinervis* pomel extract by gastric acid sufficient to preserve the bioavailability of the *A. paucinervis* pomel extract administered. The buffering agent, if used, may be administered in an amount sufficient to substantially achieve the above functionality.

Accordingly, examples of buffering agents include, but are not limited to, sodium bicarbonate, potassium bicarbonate, magnesium hydroxide, magnesium lactate, magnesium glucomate, aluminum hydroxide, aluminum hydroxide/sodium bicarbonate coprecipitate, a mixture of an amino acid and a buffer, a mixture of aluminum glycinate and a buffer, a mixture of an acid salt of an amino acid and a buffer, and a mixture of an alkali salt of an amino acid and a buffer. Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

A pharmaceutically acceptable buffering agent may comprise a bicarbonate salt of Group IA metal as a buffering agent, and may be prepared by mixing the bicarbonate salt of the Group IA metal, preferably sodium bicarbonate, with water. The concentration of the bicarbonate salt of the Group IA metal in the composition may be any concentration. By way of non-limiting example the bicarbonate concentration may range from approximately 5.0 percent to approximately 60.0 percent. The concentration of the bicarbonate salt of the Group IA metal may range from approximately 7.5 percent to approximately 10.0 percent. In one embodiment of the invention, sodium bicarbonate is the salt and is present in a concentration of approximately 8.4 percent.

In one embodiment, the amount of sodium bicarbonate 8.4% used in the solution of the present invention is approximately 1 mEq (or mmole) sodium bicarbonate per 2 mg *A. paucinervis* pomel, with a range of approximately 0.2 mEq (mmole) to 5 mEq (mmole) per 2 mg of *A. paucinervis* pomel.

In certain embodiments, enterically coated *A. paucinervis* pomel extract may be used. Alternatively, *A. paucinervis* pomel extract powder may be used. The enterically coated *A. paucinervis* pomel particles may be mixed with a sodium bicarbonate ($NaHCO_3$) solution (8.4%), which dissolves the enteric coating and forms an *A. paucinervis* pomel solution. The *A. paucinervis* pomel solution may have pharmacokinetic advantages over standard time-released *A. paucinervis* pomel extract capsules, including: (a) more rapid drug absorbance time (about 10 to 60 minutes) following administration for the *A. paucinervis* pomel solution versus about one to three hours following administration for the enteric-coated pellets; (b) the $NaHCO_3$ solution protects the *A. paucinervis* pomel from acid degradation prior to absorption; (c) the $NaHCO_3$ acts as an antacid while the *A. paucinervis* pomel is being absorbed; and (d) the solution may be administered through an existing indwelling tube without clogging, for example, nasogastric or other feeding tubes (jejunal or duodenal), including small bore needle catheter feeding tubes.

Additionally, various additives may be incorporated into the inventive solution to enhance its stability, sterility and isotonicity. Further, antimicrobial preservatives, antioxidants, chelating agents, and additional buffers may be added, such as AMBICIN®. However, microbiological evidence shows that this formulation inherently possesses antimicrobial and antifungal activity. Various antibacterial and antifungal agents such as, for example, parabens, chlorobutanol, phenol, sorbic acid, and the like may enhance prevention of the action of microorganisms.

In certain embodiments, isotonic agents, for example, sugars, sodium chloride, and the like may be included in the composition. Additionally, thickening agents such as methylcellulose may be desirable to use in order to reduce the settling of the A. paucinervis pomel extract from the suspension.

A solution may further comprise flavoring agents (e.g., chocolate, root beer or watermelon) or other flavorings stable at pH 7 to 9, and anti-foaming agents (e.g., simethicone 80 mg, MYLICON®).

Embodiments of the invention further include a pharmaceutical composition including A. paucinervis pomel extract in a form convenient for storage, whereby when the composition may be placed into an aqueous solution, the composition dissolves yielding a suspension suitable for enteral administration to a subject. The pharmaceutical composition may be in a solid form prior to dissolution or suspension in an aqueous solution. The A. paucinervis pomel extract may be formed into a tablet, capsule, pellets or granules, by methods well known to those skilled in the art.

The resultant A. paucinervis pomel extract solution may be stable at room temperature for several weeks and inhibit the growth of bacteria or fungi. The solution may maintain greater than 90% of its potency for 12 months. By providing a pharmaceutical composition including A. paucinervis pomel extract in a solid form, which may be later dissolved or suspended in a prescribed amount of aqueous solution to yield the desired concentration of A. paucinervis pomel extract, the cost of production, shipping, and storage may be greatly reduced as no liquids are shipped (reducing weight and cost), and there is no need to refrigerate the solid form of the composition or the solution. Once mixed, the resultant solution may then be used to provide dosages for a single patient over a course of time, or for several patients.

As mentioned above, the formulations of the present invention may also be manufactured in concentrated forms, such as tablets, suspension tablets and effervescent tablets or powders, such that upon reaction with water or other diluent, an aqueous form of the present invention is produced for oral, enteral, or parenteral administration.

In addition to the suspension tablet, the solid formulation of the present disclosure may be in the form of a powder, a tablet, a capsule, or other suitable solid dosage form (e.g., a pelleted form or an effervescing tablet, troche or powder), which creates a solution according to the invention in the presence of diluent or upon ingestion. For example, the water in the stomach secretions or water which is used to swallow the solid dosage form may serve as an aqueous diluent.

The pharmaceutical compositions of the present disclosure include A. paucinervis pomel extract, as the active ingredient, and may also include a pharmaceutically acceptable carrier, and optionally, other therapeutic ingredients.

In one embodiment of the invention, the A. paucinervis pomel may be administered in combination with PEG 300.

The active ingredient, for example A. paucinervis pomel, may be mixed with PEG 300 and administered to a subject.

In one embodiment of the invention, the A. paucinervis pomel extract, may be administered to a subject together with another active ingredient such as a chemotherapeutic agent. Contemplated chemotherapeutic agents include, but are not limited to, alkylating agents, such as carboplatin and cisplatin; nitrogen mustard alkylating agents; nitrosourea alkylating agents, such as carmustine (BCNU); antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide (VP-16), interferon, paclitaxel, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine. Further, the following additional drugs may also be used in combination with the A. paucinervis pomel extract and/or another chemotherapeutic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon leuprolide acetate; meperidine HCl; methadone HCl; ranitidine HCl; vinblastin sulfate; and zidovudine (AZT).

The phrase "combination therapy," as used herein, refers to co-administering an A. paucinervis pomel extract, and another chemotherapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

Combination therapy may also embrace the administration of the therapeutic agents as described above in further combination with other biologically active ingredients and non-drug therapies. Where the combination therapy further includes a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

According to one embodiment of the invention, an *A. paucinervis* pomel extract may be used in the manufacture of a medicament for the treatment of a tumor. For example, use of *A. paucinervis* pomel extract in the manufacture of a medicament for the treatment of a tumor represents one embodiment of the invention.

The compositions described herein contain a biologically active extract of the plant *Aristolochia paucinervis* pomel, which is also known as *Aristolochia Longa Paucinervis, Bourouzdoum* and *Berousdoum*. This plant is referenced herein as "*Aristolochia paucinervis* pomel" and "*A. paucinervis* pomel," while an extract is referenced herein as an "*A. paucinervis* pomel extract" and grammatical variants such as "extract of *A. paucinervis* pomel" and "extract of *Aristolochia paucinervis* pomel" are also used.

Embodiments of the present invention provide biologically active *A. paucinervis* pomel extracts and methods of making the extracts. The characteristics of the *A. paucinervis* pomel plant may include the following physical features: Stem: very ramified and ascending and having a yellowish green color; Leaf: entire, alternate, simple leaves, round of 5×5 cm approximately; Flower: flower hermaphrodites of 3-6 cm, solitary, tubular of brown color; Fruit: ovoid capsule of some 2.5 cm long that opens in six valves and produces numerous seeds; and Root: oval shaped, large, brownish in color. *A. paucinervis* pomel has been identified in many geographical areas, including Europe and Northwest of Africa, in particular in the Western Mediterranean region. Specific locations in which *A. paucinervis* pomel occurs include Morocco, Europe, for example, Spain, Algeria, and Tunisia. In certain embodiments extracts may be prepared by using plants originating in Morocco and grown in Morocco and the United States. It is expected that plants from any geographical area may be successfully grown anywhere given appropriate outdoor or indoor growing conditions.

According to one embodiment of the invention the methods for preparing an *A. paucinervis* pomel extract comprise obtaining a quantity of plant material from *A. paucinervis* pomel, optionally breaking up the plant material, contacting the plant material with an extraction medium and separating the plant material from the extraction medium. Example 1 illustrates procedures for preparing *A. paucinervis* pomel extracts using water as the extraction medium. A method of producing the *A. paucinervis* pomel plant extract according to embodiments of the invention may optionally include first breaking up the plant material in order to increase its surface area to volume ratio and to increase efficiency of the extraction process. Procedures for breaking up plant material may include grinding, chopping, blending, shredding, pulverizing, triturating, or equivalent methods. The extraction medium (solvent) may then be contacted with the plant material under conditions suitable for causing one or more biologically active phytocompounds to partition from the plant material into the extraction medium. Such conditions include, in some cases, heating the extraction medium to a temperature above room temperature, agitation, contact time, and the like. For example, temperatures for extraction may be from about 20° C. to about 80° C. Where water is the extraction solvent, the extraction temperature is generally from room temperature to about 60° C. Example 1 describes preparation of *A. paucinervis* pomel extract at about 40° C. and at about room temperature. The person of skill in the art may recognize that the proper balance should be drawn between extraction efficiency on the one hand and phytocompounds compound stability on the other.

Once the extraction medium and the plant material are combined, they are optionally agitated to ensure efficient exchange of phytocompound from the plant material into the extraction medium, and are left in contact for a time sufficient to extract a useful amount of phytocompounds from the plant material into the extraction medium. After such time has elapsed, the extraction medium containing the phytocompounds may be separated from the plant material. Such separation may be accomplished by an art-recognized method, for example filtering, decanting, and the like. Additionally, the extraction medium may be evaporated and a powdered extract may be obtained.

Thus, one embodiment of the present invention provides a method for making an extract of the plant species *Aristolochia paucinervis* pomel including obtaining a quantity of *Aristolochia paucinervis* pomel plant matter, contacting the plant matter with an extraction medium comprising water at a temperature between about 20° C. and about 40° C., and separating the extraction medium from the plant matter. The temperature may be room temperature (typically considered to be about 25° C. to about 35° C., or particularly 25° C. for convenience. The extraction medium is generally aqueous, but may include non-aqueous components if desired, for example, to enhance solubility or stability of certain phytocompounds. An aqueous extraction medium may contain, for example, buffering agents, stability promoting reagents, thickening agents and the like, and may be selected by those skilled in the art based on desired properties of the extract or processing conditions. Water is an example of the most simple aqueous extraction medium.

A composition comprising an *A. paucinervis* pomel extract prepared for administration to a subject may contain one or more forms of the extract. Forms of the extract may include, for example, liquid extract, extract powder, plant powder, plant powder prepared in about 200× concentrated water extract of the powder, fine minced powder, and the like. Example 1 describes procedures for preparing biologically active *A. paucinervis* pomel extract.

However, any suitable method involving the use of the aqueous solvent may be used to extract the water-soluble biologically active ingredients from the parts of the aforementioned plant. The extracting conditions may be carried out for a period of time sufficient to produce a liquid extract that contains about 20 wt. % of dissolved biologically active extract in the aqueous solvent. (Unless stated otherwise, "wt. %," as used herein, means percent by weight based on the total weight of the composition.) The biologically active extract comprises about 20 wt. % of the aqueous solution, for example, 20 kg of the dissolved extract in 100 L of aqueous solution. However, the liquid extract may also contain about 5 wt. %, 10 wt. %, 25 wt. %, 30 wt. % or more of dissolved biologically active extract in the aqueous solvent.

Any suitable form of a part of *Aristolochia paucinervis* pomel may be used in the extraction, for example, chunks of the part. In one form, the part of the walnut tree is dried and reduced to a powder, for example, by a grinding or pulverizing operation which involves subjecting the roots or bark of the walnut tree to grinding or crushing to particles which may vary in size over a relatively wide range. For example, a powder of fine particles may be used and the powder may be macerated with the aqueous solvent.

The aqueous solvent for use in the extraction may comprises at least about 70 wt. % water, at least about 90 wt. % water, or it may comprise about 100 wt. % water. As the concentration of water comprising the aqueous solvent is reduced, the biological effectiveness of the extract which is obtained from treatment with lower amounts of water in the aqueous solvent may be reduced.

It should be appreciated that the aqueous solvent that may be used to prepare the biologically active extract of the present invention is significantly different from saliva which is a unique composition. For example, saliva is a relatively viscous material which contains enzymes and has a pH which averages about 6 to about 6.5. Water, for example, deionized water, has a pH which averages about 4.5 to about 5, has a lower viscosity than saliva, and does not contain enzymes present in saliva.

An aqueous solvent which comprises less than about 100 percent water may include a material which functions as a co-solvent. An example of such a material is an alcohol such as, for example, ethanol or methanol. For example, the aqueous solvent may comprise about 10%, 20%, or 30% ethanol. It is noted that extracts obtained using extraction solutions containing ethanol may be different in nature from those obtained using water alone as an extraction medium. While not intending to be bound by a particular theory, the differences in such extracts could be due to hydrophobic portions of an alcohol solubilizing or stabilizing compounds which are not fully hydrophilic in nature.

The extraction may be conducted under temperature conditions which reduce the tendency of the biologically active ingredients comprising the extract to decompose. The temperature of the aqueous solvent may be about less than 60° C. and may be in the range of about 4° C. to about 20° C. When the aqueous solvent has a temperature other than ambient or room temperature (about 23° C.), refrigerating or heating equipment may be used to lower or raise the temperature of the solvent to the desired operating temperature.

The extracting conditions which involve contacting the parts of *Aristolochia paucinervis* pomel with the aqueous solvent at the desired temperature may be carried out for a period of time sufficient to produce an aqueous solution which has the desired concentration of dissolved biologically active extract, for example, about 20 wt. %. Inasmuch as the water-soluble biologically active materials which comprise the extract are present in the plant part in very small amounts, for example, less than about 10 wt. %, relatively large quantities of aqueous solvent and relatively long periods of time are needed to arrive at the desired concentration of extract in the concentrated aqueous solution that is produced by the extraction. For example, in treating the roots of *Aristolochia paucinervis* pomel, about 1000 kg of the roots may be treated over a period of about 100 days with an aqueous solvent that comprises substantially all water at a temperature of about 4° C. to produce a concentrated aqueous solution of extract that comprises about 20 wt. % of biologically active extract.

One process for providing the concentrated aqueous solution of extract involves a multi-step process in which a powder of the *Aristolochia paucinervis* pomel part is mixed with the aqueous solvent for a prolonged period of time (for example, one to two days) after which the resulting aqueous solution (hereafter "solution 1") is separated from the powder (hereafter the "powder residue") with pressing. The powder residue which contains "left-over" water-soluble active ingredients is contacted with additional aqueous solvent for a prolonged period of time (for example, one to two days) with stirring, after which the aqueous solvent is separated from the residue powder with pressing and the resulting aqueous solution containing dissolved biologically active ingredients is added to a "solution 1" (see Example 1) along with an additional amount of powder of the walnut tree part. These various steps may be repeated until the desired amount of biologically active extract is obtained. The extract in a solid powder or reduced form may be recovered from the solution by evaporating the liquid solvent. Prior to evaporation, the solution may be filtered, as may be needed, to remove therefrom solid impurities.

The invention includes within its scope the use of compounds comprising the biologically active extract, including compounds comprising synthetic forms of such compounds, that is, such compounds prepared by appropriate synthesis.

Examples 7 and 8 show that CD1 mice injected with high doses of *A. paucinervis* pomel extract intravenously for 14 repeated days or orally for 28 repeated days show no signs of toxicity as determined by gross necropsy, clinical chemistry for liver, heart and kidney function and blood composition. Moreover, Example 9 shows that *A. paucinervis* pomel extract protects Lewis rats from methotrexate-induced liver damage. In addition, Examples 5 and 6 show that *A. paucinervis* pomel extract is nontoxic to human white blood cells, red blood cells and human umbilical vein endothelial cells in vitro. In particular, *A. paucinervis* pomel extract does not induce red blood cell lysis; does not induce PBMC or PMN cytolysis, and does not effect HUVEC proliferation. Example 13 demonstrates *A. paucinervis* pomel extract is non-toxic to humans. The *A. paucinervis* pomel extracts described herein are nontoxic to animals and may have an unexpected protective effect on liver function.

Moreover, the Examples herein also demonstrate that extracts of *A. paucinervis* pomel may effectively reduce growth of tumor cells in vivo and in vitro. Specifically, Example 2 describes in vitro experiments which demonstrate that *A. paucinervis* pomel extract is capable of reducing proliferation of several tumor cell lines derived from various organs, including colon cancer cells, small cell lung cancer cells, leukemia cells, prostate cancer cells, pancreatic cancer cells, liver cancer cells, and melanoma cells. In vivo efficacy of *A. paucinervis* pomel extract is shown herein, for example, in Example 10. In one study, *A. paucinervis* pomel extract is administered to nude mice transplanted with human U87MG gioblastoma cells orthotopically in the brain (dosage was about 10 mg/kg). These studies show that treatment with *A. paucinervis* pomel extract results in a statistically significant improvement in survival of mice by over 40% for a period close to ten days. Another study shows that *A. paucinervis* pomel extract improves survival in mice transplanted intracranially with U87MG glioblastoma. A further study shows that *A. paucinervis* pomel extract improved survival of mice implanted with A431 carcinoma in a xenograft model. Notably, Examples 11 through 16 describe that *A. paucinervis* pomel extract is effective for reducing proliferation of cancer cells and improving survival of human cancer patients.

The data provided herein show that treatment of tumor-bearing animals with *A. paucinervis* pomel extract improves survival without resulting in liver toxicity. Avoidance of liver toxicity may be relevant to some cancer patients, especially those having increased susceptibility to such toxicity, for example, due to a preexisting liver condition. Examples of liver conditions include hepatic fibrosis, portal hypertension, hepatitis C infection, veno-occlusive disease, cirrhosis, type 1 glycogen storage disease, porphyria, cancer, inherited liver-related diseases such as galactosemia, tyrosinemia, thalassemia and the like. Therefore, in one embodiment of the present invention, a composition containing an *A. paucinervis* pomel extract described herein, may be used for treating cancer in a subject having liver sensitivity or susceptibility to a chemotherapeutic agent. In one embodiment of the present invention, a subject having liver sensitivity prior to treatment is identified and unwanted cell growth in the subject is treated by administering to the subject an effective amount of a plant extract composition comprising an extract of the plant species *Aristolochia paucinervis* pomel.

Additionally, avoidance of liver toxicity may reduce or prevent certain "late effects" associated with some cancer therapies. Late effects are side effects of cancer treatment that become apparent after treatment has ended. Cancer survivors sometimes experience late effects of cancer treatment a few months or years after treatment is completed. Liver problems are a type of late effect associated with chemotherapy. As a specific example, treatment for acute lymphoblastic leukemia (ALL), neuroblastoma, Wilms' tumor and other childhood cancers have been shown to cause late effects in the liver. Late effects in the liver may include, for example, hepatic fibrosis, liver failure, portal hypertension, veno-occulsive disease. In one embodiment of the present invention, a composition containing an *A. paucinervis* pomel extract may be used for treating cancer in a subject without inducing late term liver conditions. In another embodiment, a composition containing an *A. paucinervis* pomel extract may be used for treating cancer in a subject recovering from cancer or a subject having undergone a different cancer therapy.

As is described herein, a subject may be susceptible to liver toxicity for a variety of reasons including the presence of preexisting liver disease and treatment with chemotherapeutic or other agents known to induce late effects in the liver. The skilled clinician is capable of identifying patients who are susceptible to liver toxicity by performing routine laboratory tests or test panels. Examples of tests for identifying liver malfunctions may include, for example, determination of Alanine Aminotransferase ("ALT") levels. ALT is the enzyme produced within the cells of the liver. The level of ALT is abnormally increased when liver cells have been inflamed or have undergone cell death. Other tests include detection of Aspartate Aminotransferase ("AST") levels. The levels of this enzyme reflect damage to the hepatic cell. AST levels are less specific for liver disease and may be elevated by other conditions. Bilirubin is another indicator of liver damage. If the direct bilirubin levels are low, while the total bilirubin levels are high, liver cell damage or bile duct damage within the liver itself may be present. Albumin levels are another indicator of liver damage since Albumin is the major protein present within the blood and is synthesized by the liver. As such, it is a marker for the ability of the liver to synthesize proteins. A skilled clinician might also test for Prothrombin time ("PT") which is another measure of hepatic synthetic function. PT is affected by proteins synthesized by the liver. Platelet count is another test to detect liver damage. Subjects with liver disease develop a large spleen. As this process occurs, platelets are trapped within the sinusoids (small pathways within the spleen) of the spleen. While the trapping of platelets is a normal function for the spleen, in subjects with liver disease it becomes exaggerated because of the enlarged spleen (splenomegaly). Serum protein electrophoresis is also useful for evaluation of patients who have abnormal liver function since it allows a direct quantification of multiple different serum proteins.

Without being bound by any particular theory, data presented in Example 3 demonstrate that *A. paucinervis* pomel extracts may induce apoptosis in tumor cells by, for example, up-regulating the levels of the anti-tumor protein 3'-Phosphatase and Tensin Homologue ("PTEN"). It has been shown previously that PTEN induces apoptosis of tumor cells through AKT Kinase activation and production of apoptotic cytokines such as TNF-α. PTEN also down-regulates Phosphotidyl Inositol-3 Kinase ("PI-3 Kinase") activity, which results in reduced cell motility, making such cells susceptible targets for TNF-α and NK cells. As such, it its expected that an *A. paucinervis* pomel extract may be used to induce apoptosis in tumor cells for in vivo therapeutic methods as well as in vitro research and/or treatment methods.

The use of an *A. paucinervis* pomel extract to inhibit growth of tumor cells has been demonstrated herein in several types of tumor cells in vitro. Example 2 describes that *A. paucinervis* pomel extract may inhibit proliferation or induce cell death in tumor cells derived from colon cancer, small cell lung cancer, leukemia, prostate cancer, pancreatic cancer, liver cancer, and melanoma. It is expected that other types of tumor cells may respond similarly to *A. paucinervis* pomel extract. Example 4 describes that *A. paucinervis* pomel extract may enhance the function of resting T cells. As such, a composition containing an *A. paucinervis* pomel extract as described herein may have the effects of stimulating the ability of the immune system to attack tumor cells while also inhibiting tumor cell growth.

Therefore, the invention includes methods for treating a subject having a medical indication characterized by unwanted cell growth, in particular, cancer. In an embodiment, the invention provides for a method of reducing cell growth in a subject, involving administering to the subject an effective amount of a composition comprising an extract of the plant species *Aristolochia paucinervis* pomel.

A composition of the invention may be used as a chemotherapeutic agent, as well as an agent for reducing or preventing liver toxicity while having no adverse effect on the effectiveness of another chemotherapeutic agent. The compositions of the invention may be used together with other therapeutic modes for treating cancer, such as an adjuvant to conventional modes of anticancer therapy such as radiotherapy and chemotherapy. Therefore, based on results described herein, for example, in Examples 10-16, the invention provides a method of increasing the likelihood of survival of a subject having cancer, comprising administering to the subject an effective amount of a plant extract composition, comprising an extract of the plant species *Aristolochia paucinervis* pomel.

The *A. paucinervis* pomel compositions of the invention also may be used to promote a sense of general well being and to increase the vitality in patients diagnosed as having any type of cancer, to increase the appetite, restore health and increase the lifespan of patients diagnosed as having any type of cancer; to improve the ambulatory capacity in patients diagnosed as having any type of cancer; to activate the nervous system, prevent degenerative changes, stimulate regeneration and improve the psychological status in patients diagnosed as having any type of cancer, and to stimulate metabolism, accelerate anabolism, promote catabolism thereby flushing the body of toxic metabolites and reducing the side effects of chemotherapy and radiotherapy. Contemplated methods of treating cancer include administering the extract of the invention alone, in combination with, or in sequence with, such other compounds.

Procedures for determining the efficacy of cancer therapy are widely known. Such procedures may be general in nature, applicable to many types of cancer, or specific for a particular cancer. As a non-limiting example of a procedure for determining objective tumor response by CT scan, see Miller et al.

1981, Reporting Results of Cancer Treatment, Cancer 47, 207-214, the contents of which are incorporated herein by reference. Evaluation may be performed at various stages during treatment of a patient, typically at baseline, week 4, week 8 and at the end of three months. Lesions may be reviewed and evaluated for response as one or more of complete response, partial response, stable disease, or progressive and progression-free survival.

The following examples are intended to illustrate but not limit the present invention.

Example 1

Preparation of A. paucinervis Pomel Extract

In a first non-limiting example of preparing A. paucinervis pomel extract, roots of the Aristolochia paucinervis pomel plant were converted to an un-extracted powder by crushing or grinding prior to being treated with water. Briefly, 20 kilograms of the un-extracted powder were added to 100 liters of water and the mixture was agitated for one hour at 40° C. After the one hour agitation, an extract of Aristolochia paucinervis pomel and a residual powder was formed. The liquid was separated from the residual powder—this is referenced as cycle 1. Next, 20 kilograms of additional un-extracted powder was added to the liquid extract from cycle 1 and allowed to agitate for one hour at 40° C. This process was repeated 200 times. The solution was filtered to remove particulate matter and then the extract was recovered in a solid powder form from the solution by evaporating the liquid. An aqueous solution was prepared containing 176.2 mg dried A. paucinervis pomel extract/ml, at pH 6.0. This solution was found to be stable at −80° C. for over eight months as tested by its MTT activity on cancer cell in vitro. The crude powder form of A. paucinervis pomel extract was found to be stable for over one year at −80° C., as tested by extracting the active component as described above and testing in in vitro MTT activity assays using cancer cells.

In a second non-limiting example of preparing A. paucinervis pomel extract, A. paucinervis pomel plant material was suspended at a concentration of 12.5% (w/v) in ultra-pure water (resistance=18.2 megaohm-cm) and mixed by rocking for 10 minutes at room temperature. The extracts were then separated from the swelled plant material by vacuum filtration through Whatman Grade Number 3 (Whatman, Inc., Florham Park, N.J.) qualitative filter paper. The volume of the recovered extract was measured and fresh A. paucinervis pomel plant material added to yield a final concentration of 12.5%. The extraction process was repeated for a total of 5 or 9 times. The extracts were then aliquotted and the aliquots were stored at −80° C.

In a third non-limiting example of preparing A. paucinervis pomel extract, dried A. paucinervis pomel plant material was extracted with water at room temperature for 10 minutes and the extract was clarified by centrifugation and filtration. This process was repeated using the clarified extracts as solvent a total of 5, 9 or 200 times to generate extracts with final relative concentrations of 5×, 9× and 200×, respectively. The 9× extract served as starting material for fractionation via reverse-phase HPLC analysis using a preparative C18 column. One ml of the 200× extract, at pH 6.0, was dried under vacuum at 38° C. in a flask of known weight using a rotovap concentrator. Residual amounts of liquid were removed by placement of the flask in a vacuum dessicator for three days. The flask containing the dried solid was then weighed using an analytical balance. The weight of the solid material (a sticky film coating the flask), was determined to be 176.2 mg. The original stock compound (200X=176.2 mg/ml) is dark brown in color and is mainly clear.

Figure 1B:
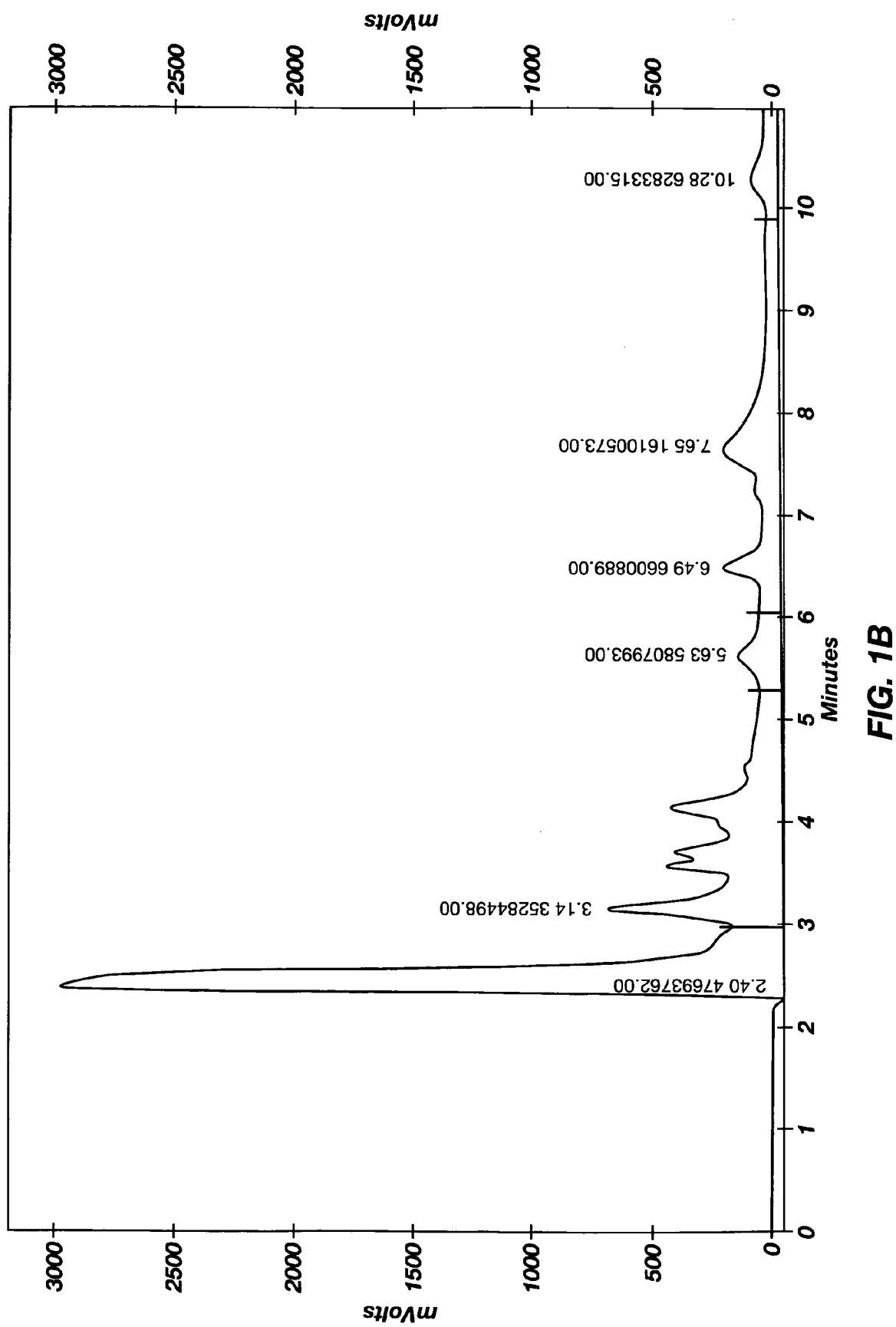
Figure 1C:
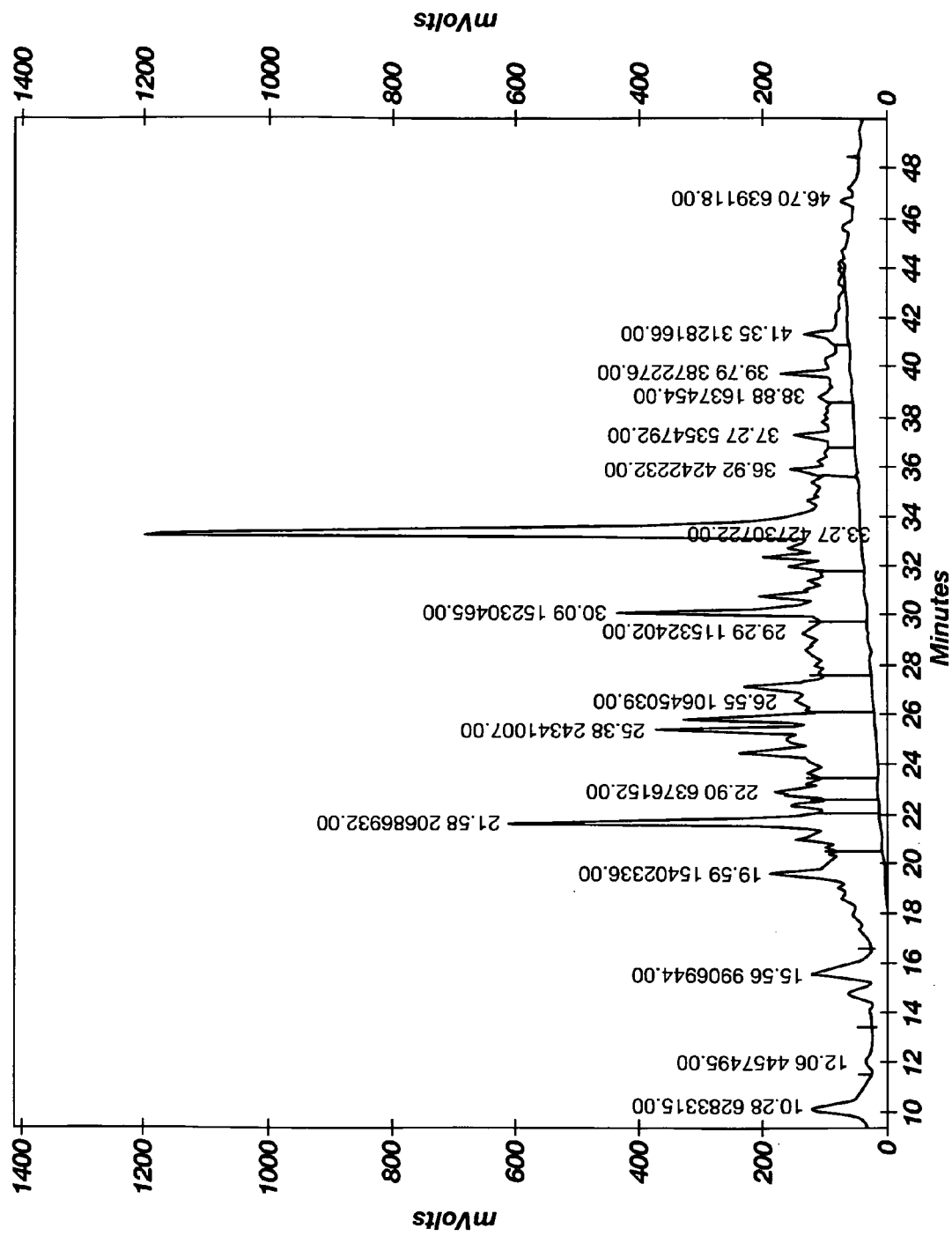
Figure 1D:
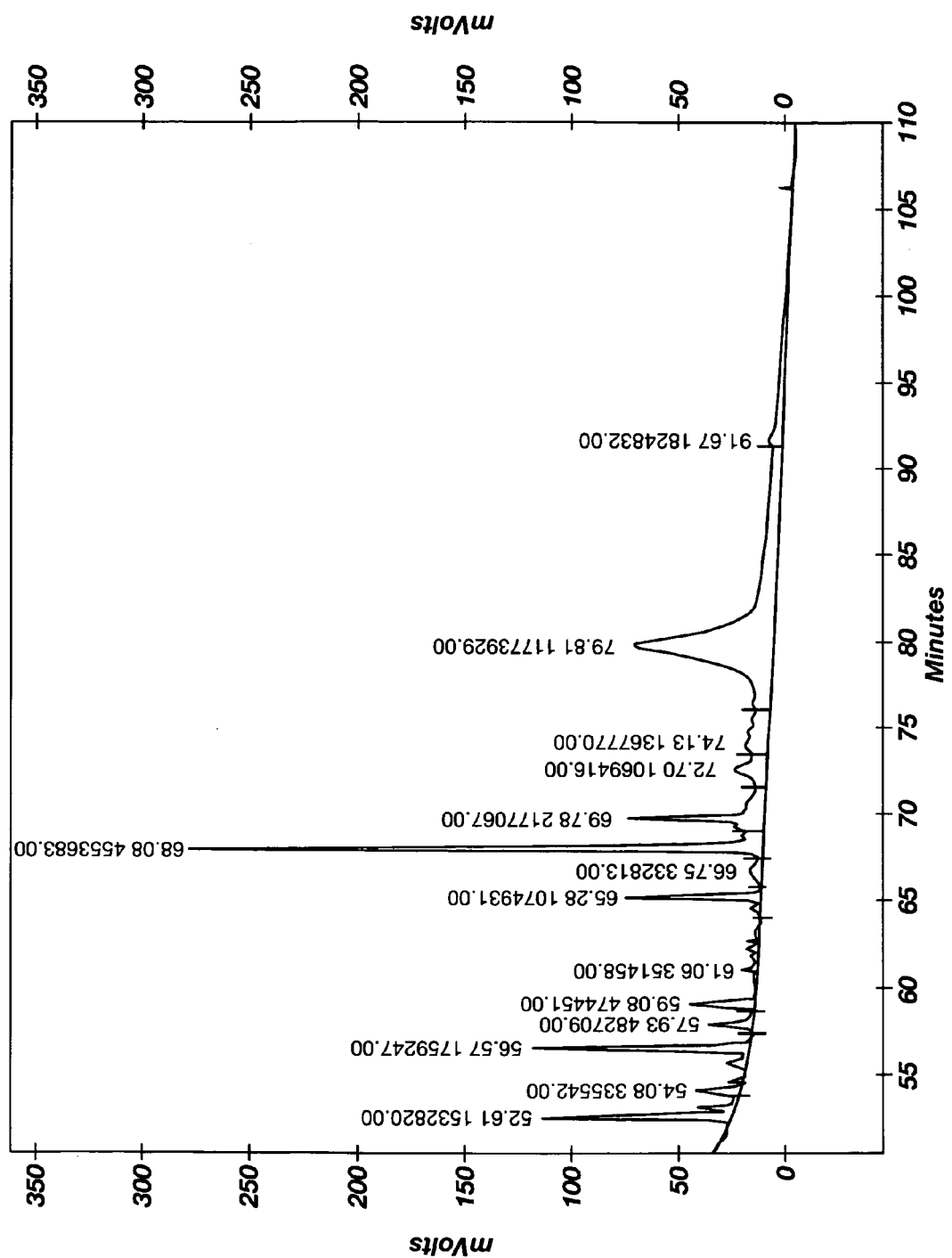

HPLC, UV absorption analysis and mass spectrometry analysis were employed for characterizing the resultant A. paucinervis pomel extract. Reversed-phase analytical HPLC analyses of the A. paucinervis pomel extracts were performed on a C18 column (4.6×250 mm, VYDAC-C18, 15-20 micron particle size, 300 Angstrom pore size) employing a 0-60% acetonitrile gradient on a background of 0.05% TFA for 100 minutes after a 10-minute elution in 0.05% TFA. The UV absorption profiles at 210 and 254 nM of the fractionated materials were generated. FIGS. 1A, 1B, 1C and 1D show results of high performance liquid chromatography (HPLC) analysis using a C18 column and detecting at 210 nm. FIG. 1A shows elution from 1 to 110 minutes, while FIGS. 1B, 1C and 1D show amplified portions of the trace.

In a fourth non-limiting example of preparing A. paucinervis pomel extract, the same methodology as described in the third non-limiting example was employed to fractionate 1.5 ml of the 9× A. paucinervis pomel extract using a larger preparative column (50×350 mm, VYDAC-C18, 15-20 micron particle size, 300 Angstrom pore size). The weight of the dry 200× was 176 mg/ml (586 nM), the 9× is 7.9 mg/ml (26.3 nM) and the 5× is 4.4 mg/ml (14.6 nM). It was also determined that the extract contains both hydrophobic and hydrophilic molecules with molecular weights ranging from the low 100 to high 700 Da.

In yet other embodiments for preparing a concentrated aqueous extract involves a multi-step process in which a powder of the A. paucinervis pomel plant part is mixed with the aqueous solvent for a prolonged period of time (for example, one to two days) after which the resulting aqueous solution (hereafter "solution 1") is separated from the powder (hereafter the "powder residue") with pressing. The powder residue which contains "left-over" water-soluble active ingredients is contacted with additional aqueous solvent for a prolonged period of time (for example, one to two days) with stirring, after which the aqueous solvent is separated from the residue powder with pressing and the resulting aqueous solution containing dissolved biologically active ingredients is added to aforementioned "solution 1" along with an additional amount of powder of the A. paucinervis pomel plant part. One or more of these steps may be repeated until the desired amount of biologically active extract is obtained. The extract in a solid powder form may be recovered from the solution by evaporating the liquid solvent. Prior to evaporation, the solution may be filtered, as needed, to remove solid impurities. In a non-limiting example, about 1000 kg of plant material may be treated over a period of about 100 days using water as an extraction solution at a temperature of about 4° C. to produce a concentrated aqueous extract.

These preparations of A. paucinervis pomel extract may be modified to suit particular operating temperatures, time restraints and volumes, as well as available parts of the A. paucinervis pomel plant.

Example 2

Cellular Activity of A. paucinervis Pomel Extract in Human Tumor Cells In Vitro

The ability of A. paucinervis pomel extracts to inhibit the proliferation and/or to induce the cytolysis of cancer cell lines was tested using the MTT cytotoxicity assay by methods known in the art.

All cancer cell lines were obtained from the American Tissue Type Collection (ATTC, Manassas, Va.) and were cultured according to ATTC recommendations. Culture reagents, including fetal bovine sera, RPMI-1640, Dulbeco's modified Eagle's medium, McCoy's medium, minimum essential media, 1-glutamine sodium pyruvate, HEPES, penicillin/streptomycin and non-essential amino acids were obtained from Sigma Chemical Co. (St. Louis, Mo.).

Adherent cancer cells were detached from their culture vessels by brief trypsinization, resuspended at a concentration of $1\times10^5$/ml in the appropriate complete media supplemented with 50 mM HEPES and plated into the wells of a 96-well culture plate (200 µl/well: 20,000/well). The cells were then cultured overnight at 37° C. under 5% $CO_2$ to allow full adhesion and recovery before the addition of extract. Cells grown in suspension were plated at a density of 50,000 cells/well in 200 µl and allowed to recover for two hours prior to the addition of extract.

All extracts were filtered through low binding nitroacetate filters (0.22 µm pores) prior to dilution and addition to the assay plates. Extracts, HPLC fractions or their serial dilutions (made with sterile water) were added to each well in a volume of 22.2 µl and the plates cultured for 48 hours at 37° C./5% $CO_2$. For the adherent populations, the media was then aspirated from each well and the cells washed once with DPBS. The plates containing suspension cells were first centrifuged at 2,000×g for 10 minutes prior to the aspiration of the culture media (suspension cells were not washed with DPBS). Two hundred µl of fresh media containing 0.863 mg/ml thiazolyl blue tetrazolium bromide (MTT, Sigma Chemical Co.) was then added to the wells of both adherent and suspension cultures and the cells cultured for an additional four hours. The culture plates were then centrifuged at 2,000×g for 10 minutes, the media carefully aspirated from the wells, and the well contents solubilized in 200 µl of DMSO. The optical density (O.D.) at 560 nm of each well was measured using a microtiter plate reader. In each experiment, duplicate or triplicate determinations were averaged and the mean background value (determined from wells receiving media lacking MTT) subtracted. The data was then normalized to the value obtained for wells receiving sterile water and are presented a % of viability.

Cancer cells were cultured in the presence of serial dilutions of the 5× (4.4 mg/ml) *A. paucinervis* pomel extract for 48 hours, at which point the media was removed and fresh media containing MTT added. After four hours of additional culture, the resultant formazan crystals were dissolved in DMSO and the absorbance of each well measured at 560 nm. The results obtained from triplicate wells were averaged, corrected for background and then normalized to the mean value obtained from culture wells receiving water. The approximate, relative GI50 values were estimated from the graphs and are ranked in Table 1.

TABLE 1

| Cell Line | Type | $GI_{50}$ (conc. Rel. to a 1X Extract) | $GI_{50}$ (dilution) |
|---|---|---|---|
| HT-29 | Colon | 0.042 | 37.9 µg/ml |
| NCI-H1688 | Lung (small cell) | 0.06 | 53.0 µg/ml |
| COLO-205 | Colon | 0.090 | 80.0 µg/ml |
| MOLT-4 | T Cell | 0.103 | 112.8 µg/ml |
| DU145 | Prostate | 0.128 | 112.8 µg/ml |
| Jurkat | T Cell | 0.137 | 118.9 µg/ml |
| COLO-205 | Colon | 0.167 | 146.7 µg/ml |
| Panc-1 | Pancreas | 0.23 | 200.0 µg/ml |
| HCT-116 | Colon | 0.25 | 220.0 µg/ml |
| HepG2 | Liver | 0.39 | 338.5 µg/ml |
| CAKI-1 | Renal | 0.48 | 440.0 µg/ml |
| CaC02 | Colon | >0.5 | <440 µg/ml |

TABLE 1-continued

| Cell Line | Type | $GI_{50}$ (conc. Rel. to a 1X Extract) | $GI_{50}$ (dilution) |
|---|---|---|---|
| MCF-7 | Breast | >0.5 | <440 µg/ml |
| 786-O | Renal | >0.5 | <440 µg/ml |
| SK-MEL-2 | Melanoma | >0.5 | <440 µg/ml |

Figure 6A:
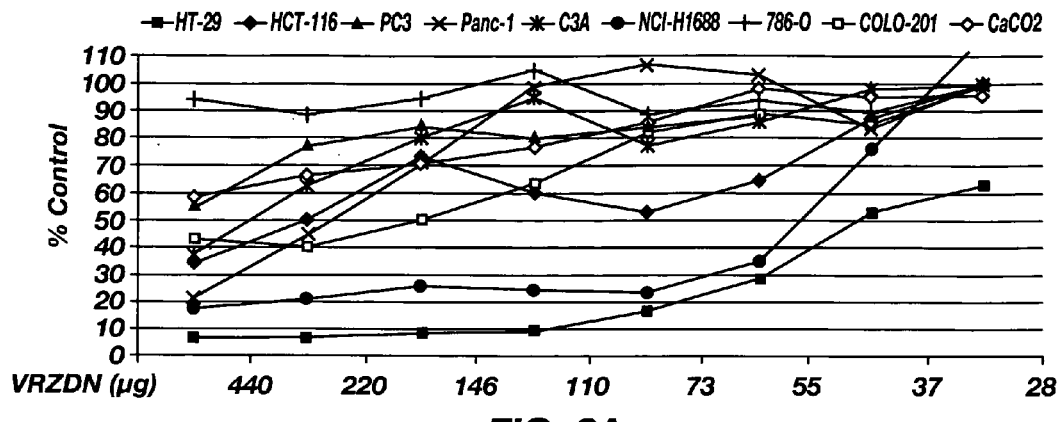
FIGS. 6A and 6B show the effect of various concentrations of *A. paucinervis* pomel extract (VRZDN) on cytolysis of various cell lines.
Figure 6B:
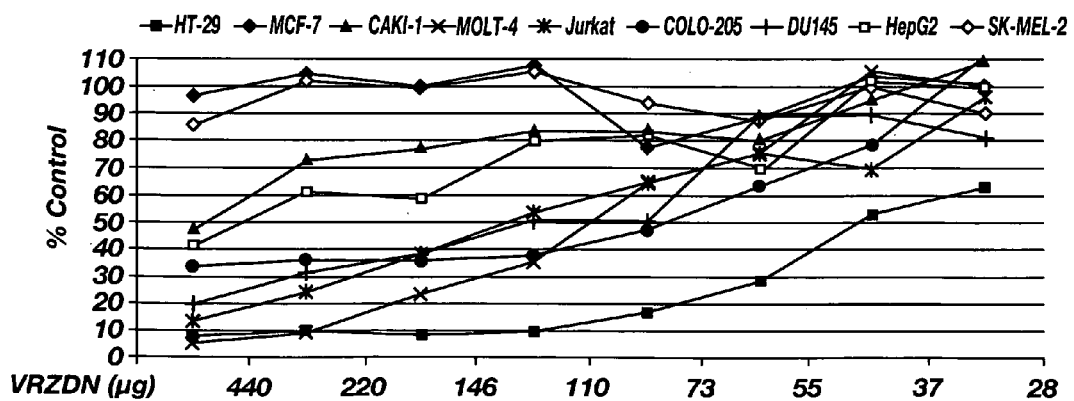
Figure 6C:
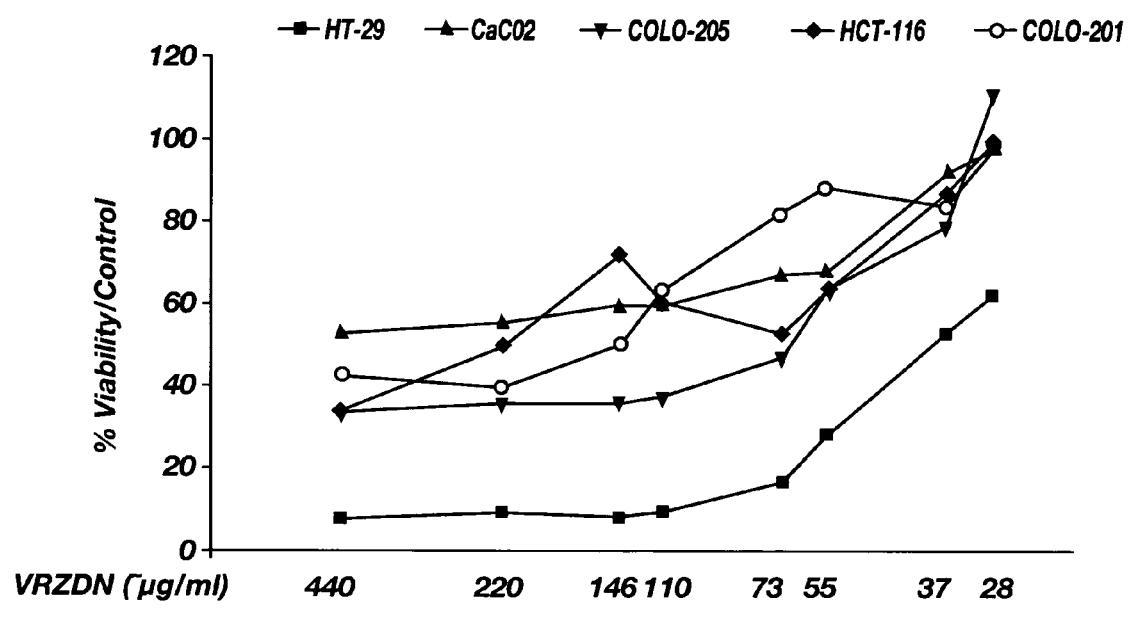
FIG. 6C shows the effects of *A. paucinervis* pomel extract on survival of various colon cancer cell lines.

From the cell lines tested, HT-29 was the most sensitive to the effect of *A. paucinervis* pomel extract, exhibiting half-maximal inhibition at about 37.9 µg/ml (FIGS. 6A and 6B). Because HT-29 is a colon cancer cell line, the effect of *A. paucinervis* pomel extract on several colon cancer cells was then examined. Results in FIG. 6C show that *A. paucinervis* pomel extract highly affected the growth of HT-29 followed by COLO-205, COLO-201, HCT-116 and then CaCO2.

These studies show that *A. paucinervis* pomel extract may effectively reduce proliferation of cultured cells derived from tumors having a variety of tissue origins.

Example 3

Figure 2:
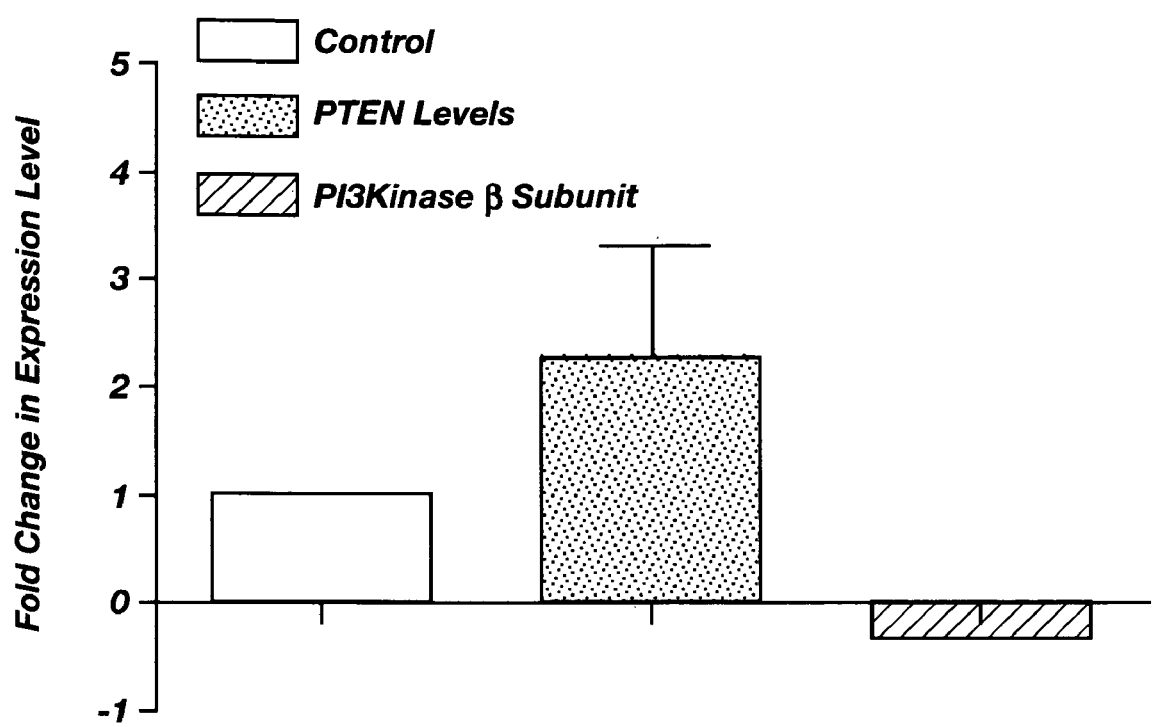
FIG. 2 shows the effects of an *A. paucinervis* pomel extract on PTEN and PI3Kinase levels in cultured human cancer cells.

Mechanism of Action of *A. paucinervis* Pomel Extract in Human Tumor Cell Apoptosis Microarray experiments were performed to evaluate the molecular pathways modulated by *A. paucinervis* pomel extract. Cell lines were treated with *A. paucinervis* pomel extract and microarray analysis was performed. Expression levels of many transcripts were compared, and this analysis indicated that *A. paucinervis* pomel extract down-regulated and up-regulated a variety of transcripts (see Table 2 below). In particular, the expression of the catalytic and regulatory subunits of phosphoinositide 3 kinases (PI3Ks) was up-regulated. In addition, as is shown in FIG. 2, *A. paucinervis* pomel extract was found to decrease cellular expression of PI3K beta subunit. Although not wishing to be limited to a particular theory, because PI3Ks are known to activate protein kinase D (PKD or AKT), a known anti-apoptotic molecule, it is hypothesized that *A. paucinervis* pomel extract induces apoptosis of tumor cell lines. Intriguingly, this effect of *A. paucinervis* pomel extract appears to be selective for certain cancer cells.

In addition to inhibiting PI3Ks expression, *A. paucinervis* pomel extract increases the expression of 3'-Phosphatase and Tension Homologue (PTEN). PTEN is known to regulate the PI3K-dependent cell motility. Hence, a combination of inhibiting PI3K and an increase in PTEN expression may lead to reduced cancer cell motility. Consequently, *A. paucinervis* pomel extract may have a role in regulating angiogenesis processes, hence, inhibiting metastatic processes. This is supported by the finding that *A. paucinervis* pomel extract reduces the transcript expression of matrix metalloproteinase (MMP1). MMP1 is important for the transendothelial migration of cancer cells. Again, this effect is selective for certain cancer cells. Results of the microarray study are shown in Table 2.

Figure 3A:
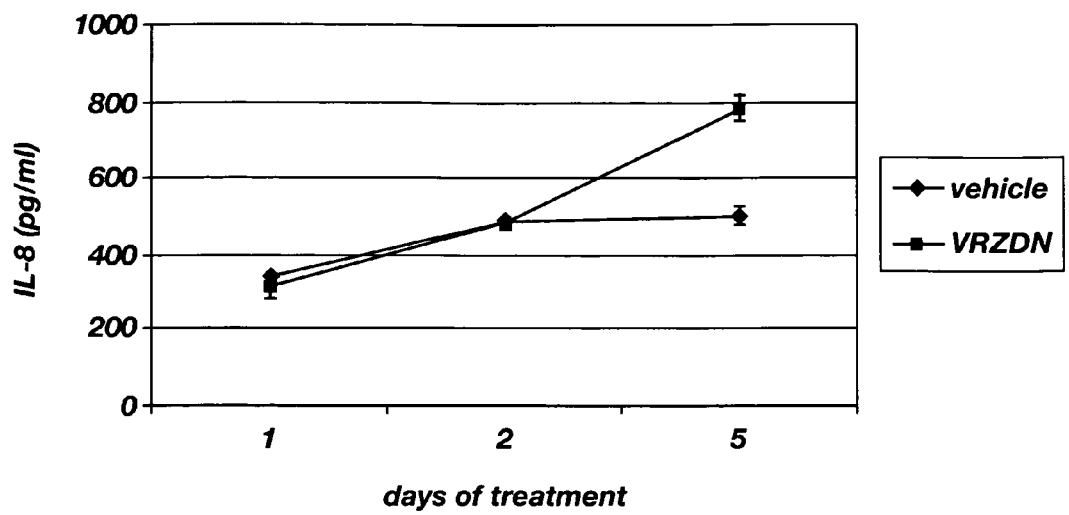
FIGS. 3A and 3B show the effects of an *A. paucinervis* pomel extract (VRZDN) on IL-8 levels in human cancer cells and on TNF-$\alpha$ levels in human cancer cells.

*A. paucinervis* pomel extract was found to increase secretion of IL-8 in the colon cancer cell line HT-29. Although not wishing to be bound by theory, *A. paucinervis* pomel extract, by promoting the release of IL-8 from HT-29, may have a role in recruiting neutrophils, which in turn may selectively kill colon cancer cells. To explain the theory, IL-8 is a robust chemoattractant for neutrophils. Recent literature reports indicate that neutrophils may have anti-tumor activity. The data described herein indicates that neutrophils may have selectivity against colon cancer cells. FIG. 3A shows the effect of *A. paucinervis* pomel extract (3.52 mg/ml) on the level of secretion of IL-8 from HT-29 cells after incubation between two and five days. As shown in FIG. 3A, IL-8 secretion levels are increased in HT-29 cells after two days of incubation with *A. paucinervis* pomel extract.

Figure 3B:
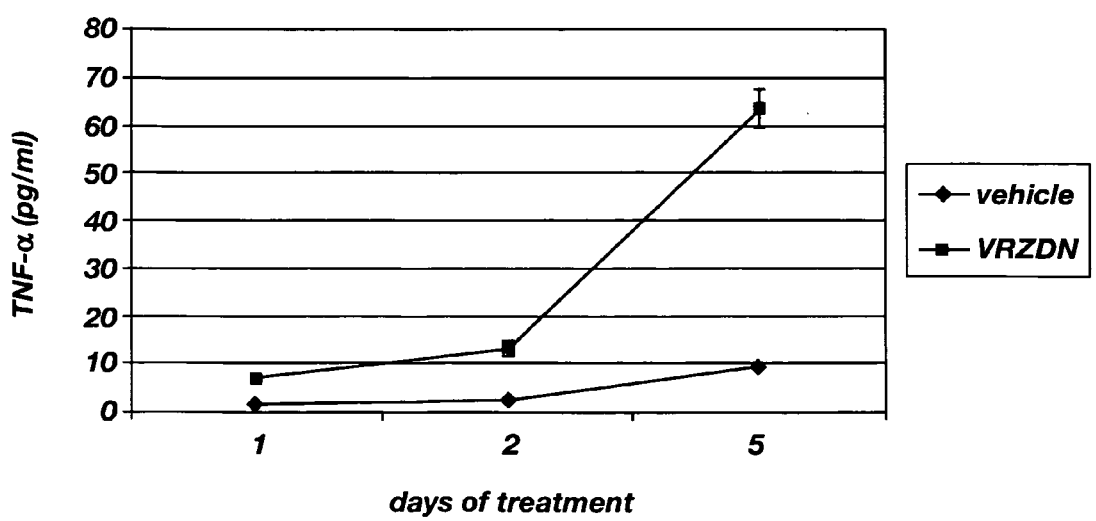
Figure 12A:
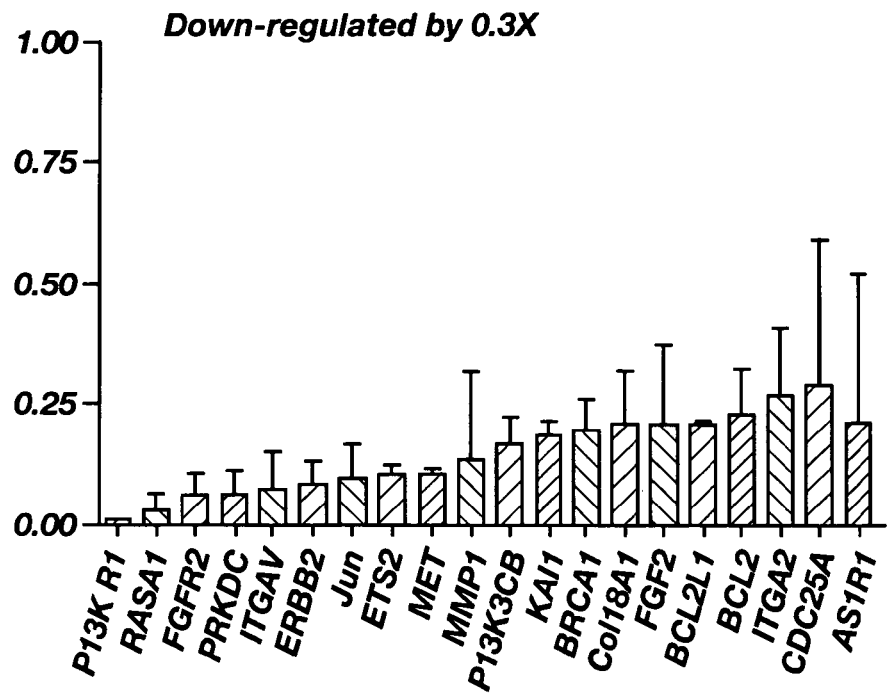
FIGS. 12A and 12B show that *A. paucinervis* pomel extract down-regulates the expression of various gene transcripts in HT-29 cells.
Figure 12B:
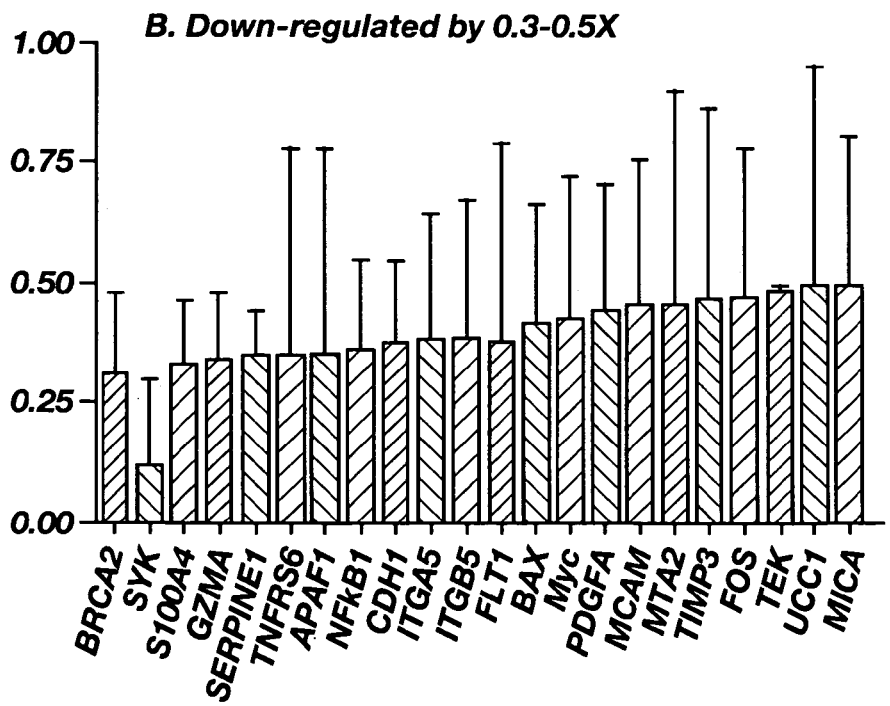
Figure 13A:
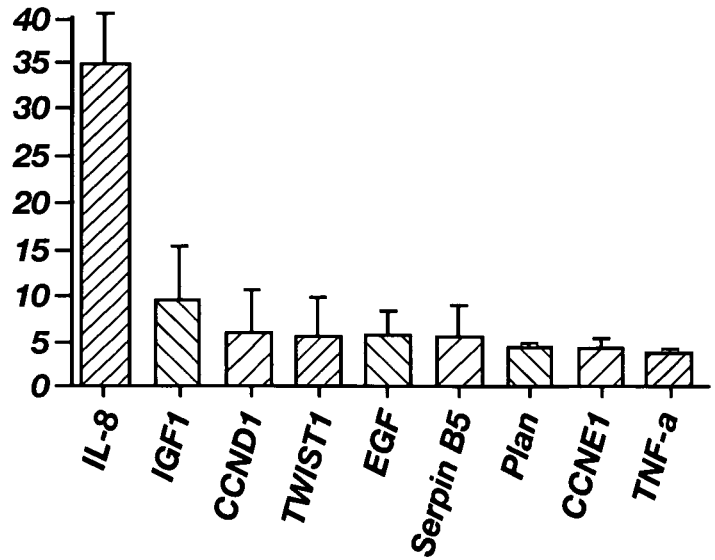
FIGS. 13A and 13B show *A. paucinervis* pomel extract up-regulates the expression of various gene transcripts in HT-29 cells.
Figure 13B:
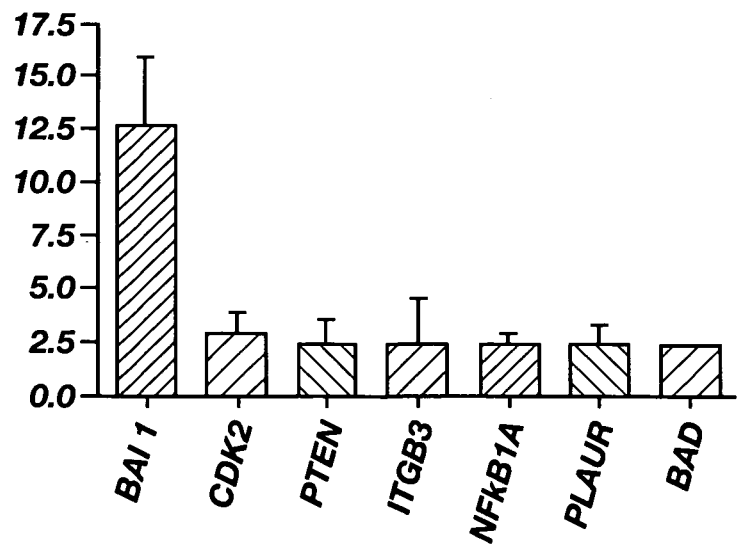

*A. paucinervis* pomel extract was also found to increase the secretion of TNF-alpha by HT-29 cells after a five-day incubation, as compared to HT-29 cells treated with vehicle. The increase in the secretion of this cytokine after incubating HT-29 cells with *A. paucinervis* pomel extract occurred after two days. FIG. 3B shows the effect of *A. paucinervis* pomel extract (3.52 mg/ml) on the level of secretion of TNF-alpha from HT-29 cells after incubation between two and five days. The increase in the secretion of this cytokine may have a role in *A. paucinervis* pomel extract anti-tumor activity. *A. paucinervis* pomel extract also increased the transcripts for these cytokines in HT-29 cells by more than three times the normal expression. FIG. 12A shows additional transcripts that are down-regulated by about 0.3 fold, whereas in FIG. 12B, shown are additional transcripts that are down-regulated by 0.3-0.5 fold. FIG. 13A, shows additional transcripts are up-regulated by three fold or more, whereas in FIG. 13B transcripts shown are additional transcripts which are up-regulated two to three fold.

These studies show that *A. paucinervis* pomel extract modulate expression of a variety of cellular transcripts and signaling molecules and exerts cellular effects on secretion of cytokines such as IL-8 and TNF alpha.

TABLE 2

| Gene name | A. Longa pomer Run #1 | A. Longa pomer Run #2 | Vehicle1 (phosphate buffer at pH 7.4) | Vehicle2 (phosphate buffer at pH 7.4) |
|---|---|---|---|---|
| RPS27A | 65535 | 65535 | 1 | 1 |
| AKT1 | 30368.42 | 46359.39 | 1.53 | 1.53 |
| ANGPT1 | 1432.722 | 1120.944 | 0.78 | 0.78 |
| ANGPT2 | 959.3889 | 478.7222 | 0.5 | 0.5 |
| APAF1 | 1231.222 | 803.9444 | 0.65 | 0.65 |
| ATM | 65022.83 | 60890.83 | 0.94 | 0.94 |
| BAD | 1417.222 | 2923.611 | 2.06 | 2.06 |
| BAI1 | 160.3333 | 793.6667 | 4.95 | 4.95 |
| BAX | 4568.639 | 1070.444 | 0.23 | 0.23 |
| BCL2 | 745.6111 | 214.2222 | 0.29 | 0.29 |
| BCL2L1 | 26163.89 | 5449.111 | 0.21 | 0.21 |
| BIRC5 | 62675.78 | 52742.14 | 0.84 | 0.84 |
| BRCA1 | 7406.889 | 1064.222 | 0.14 | 0.14 |
| BRCA2 | 374.5556 | 160.7778 | 0.43 | 0.43 |
| CASP8 | 425.2222 | 850.4444 | 2 | 2 |
| CASP9 | 374.1667 | 213.7778 | 0.57 | 0.57 |
| CCND1 | 53.44444 | 481.1111 | 9 | 9 |
| CCNE1 | 9518.167 | 39958.92 | 4.2 | 4.2 |
| CD44 | 6604.833 | 2744.389 | 0.42 | 0.42 |
| CDC25A | 907.1667 | 53.44444 | 0.06 | 0.06 |
| CDH1 | 846.8333 | 214.2222 | 0.25 | 0.25 |
| CDK2 | 13660.33 | 46508.08 | 3.4 | 3.4 |
| CDK4 | 65535 | 65535 | 1 | 1 |
| CDKN1A | 37250.58 | 65535 | 1.76 | 1.76 |
| CDKN1B | 5254.278 | 5368.25 | 1.02 | 1.02 |
| CDKN2A | 6043.944 | 5483.722 | 0.91 | 0.91 |
| CFLAR | 478.2778 | 797.3889 | 1.67 | 1.67 |
| CHEK2 | 478.2778 | 482.3333 | 1.01 | 1.01 |
| COL18A1 | 9788.944 | 1160.444 | 0.12 | 0.12 |
| CTNNB1 | 882.1111 | 427.6667 | 0.48 | 0.48 |
| E2F1 | 38423.97 | 65535 | 1.71 | 1.71 |
| EGF | 267.6667 | 1915.5 | 7.16 | 7.16 |
| EGFR | 2492.111 | 2148.917 | 0.86 | 0.86 |
| ERBB2 | 22524.89 | 1120.889 | 0.05 | 0.05 |
| ETS2 | 2353.5 | 213.7778 | 0.09 | 0.09 |
| FGF2 | 639.4444 | 53.44444 | 0.08 | 0.08 |
| FGFR2 | 6100.278 | 533 | 0.09 | 0.09 |
| FLT1 | 160.3889 | 107.3333 | 0.67 | 0.67 |
| FOS | 59079.44 | 14050.56 | 0.24 | 0.24 |

TABLE 2-continued

| Gene name | A. Longa pomer Run #1 | A. Longa pomer Run #2 | Vehicle1 (phosphate buffer at pH 7.4) | Vehicle2 (phosphate buffer at pH 7.4) |
|---|---|---|---|---|
| GZMA | 856.9444 | 375 | 0.44 | 0.44 |
| HGF | 909.6111 | 267.2778 | 0.29 | 0.29 |
| HTATIP2 | 31105.47 | 50296.89 | 1.62 | 1.62 |
| ICAM1 | 535.3889 | 906.7778 | 1.69 | 1.69 |
| IFNA1 | 428.8889 | 213.8333 | 0.5 | 0.5 |
| IFNB1 | 695.7778 | 685.8889 | 0.99 | 0.99 |
| IGF1 | 268.1111 | 1483.889 | 5.53 | 5.53 |
| IL8 | 946.5556 | 42903.86 | 45.33 | 45.33 |
| ITGA1 | 1055.222 | 268.1111 | 0.25 | 0.25 |
| ITGA2 | 1168.722 | 424.8333 | 0.36 | 0.36 |
| ITGA3 | 60871.28 | 23385.86 | 0.38 | 0.38 |
| ITGA4 | 160.3333 | 374.6111 | 2.34 | 2.34 |
| ITGA5 | 532.1667 | 107.3333 | 0.2 | 0.2 |
| ITGA6 | 8291.389 | 106.8889 | 0.01 | 0.01 |
| ITGAV | 0 | 53.44444 | | |
| ITGB1 | 54565.22 | 51769.72 | 0.95 | 0.95 |
| ITGB3 | 160.7778 | 589.7222 | 3.67 | 3.67 |
| ITGB5 | 50564.5 | 8571.111 | 0.17 | 0.17 |
| JUN | 28424.89 | 1121.444 | 0.04 | 0.04 |
| KAI1 | 2129.722 | 375.0556 | 0.18 | 0.18 |
| KISS1 | 213.7778 | 214.2222 | 1 | 1 |
| MAP2K1 | 49166.67 | 37992.83 | 0.77 | 0.77 |
| MAPK14 | 589.2778 | 1498.528 | 2.54 | 2.54 |
| MCAM | 321.1111 | 214.2222 | 0.67 | 0.67 |
| MDM2 | 267.6667 | 797.4444 | 2.98 | 2.98 |
| MET | 2972.944 | 321.5556 | 0.11 | 0.11 |
| MICA | 375.4444 | 267.2778 | 0.71 | 0.71 |
| MMP1 | 750.4444 | 0 | 0 | 0 |
| MMP2 | 8072.389 | 4833.833 | 0.6 | 0.6 |
| MMP9 | 735.2778 | 214.2222 | 0.29 | 0.29 |
| MTA1 | 1333.278 | 1228.389 | 0.92 | 0.92 |
| MTA2 | 374.6111 | 53.44444 | 0.14 | 0.14 |
| MTSS1 | 267.7222 | 106.8889 | 0.4 | 0.4 |
| MYC | 32335.89 | 8184.056 | 0.25 | 0.25 |
| NCAM1 | 853.7222 | 881.7222 | 1.03 | 1.03 |
| NFKB1 | 12875.94 | 2941.333 | 0.23 | 0.23 |
| NFKBIA | 17778.56 | 37756.69 | 2.12 | 2.12 |
| NME1 | 65031.39 | 65534.94 | 1.01 | 1.01 |
| NME4 | 25297.58 | 33717.03 | 1.33 | 1.33 |
| PDGFA | 3480.222 | 743.8889 | 0.21 | 0.21 |
| PDGFB | 8581.556 | 6035.833 | 0.7 | 0.7 |
| PIK3CB | 2242.5 | 267.6667 | 0.12 | 0.12 |
| PIK3R1 | 21375.36 | 214.2222 | 0.01 | 0.01 |
| PLAU | 1964.833 | 8221.694 | 4.18 | 4.18 |
| PLAUR | 14259.89 | 39397.53 | 2.76 | 2.76 |
| PNN | 45741.06 | 63389.78 | 1.39 | 1.39 |
| PRKDC | 21558.61 | 374.5556 | 0.02 | 0.02 |
| PTEN | 1483.667 | 4462.5 | 3.01 | 3.01 |
| RAF1 | 3793.556 | 3115.111 | 0.82 | 0.82 |
| RASA1 | 14581.67 | 160.3333 | 0.01 | 0.01 |
| RB1 | 22175.39 | 14210.78 | 0.64 | 0.64 |
| S100A4 | 26142.72 | 6183.222 | 0.24 | 0.24 |
| SERPINB2 | 745.5556 | 160.3333 | 0.22 | 0.22 |
| SERPINB5 | 2885.667 | 21819.56 | 7.56 | 7.56 |
| SERPINE1 | 374.6111 | 106.8889 | 0.29 | 0.29 |
| SNCG | 65064.94 | 60527.17 | 0.93 | 0.93 |
| SRC | 5074.306 | 1596.833 | 0.31 | 0.31 |
| SYK | 482.3333 | 213.7778 | 0.44 | 0.44 |
| TEK | 621.0556 | 261.5556 | 0.42 | 0.42 |
| TERT | 3033.472 | 1682 | 0.55 | 0.55 |
| TGFB1 | 1542.944 | 1010.889 | 0.66 | 0.66 |
| TGFBR1 | 214.2222 | 107.3333 | 0.5 | 0.5 |
| THBS1 | 582.3333 | 1118.167 | 1.92 | 1.92 |
| THBS2 | 428.5 | 588.4444 | 1.37 | 1.37 |
| TIMP1 | 65490.44 | 63926 | 0.98 | 0.98 |
| TIMP3 | 589.2778 | 107.3333 | 0.18 | 0.18 |
| TNF | 160.3889 | 482.7778 | 3.01 | 3.01 |
| TNFRSF10B | 48516.56 | 37839.47 | 0.78 | 0.78 |
| TNFRSF1A | 11648.94 | 5579.5 | 0.48 | 0.48 |
| TNFRSF25 | 6359 | 4238.778 | 0.67 | 0.67 |
| TNFRSF6 | 1099.194 | 53.44444 | 0.05 | 0.05 |
| TP53 | 5028.333 | 3507.889 | 0.7 | 0.7 |
| TWIST1 | 160.7778 | 1331.611 | 8.28 | 8.28 |
| UCC1 | 321.1667 | 53.44444 | 0.17 | 0.17 |
| VEGF | 481.8889 | 1067.111 | 2.21 | 2.21 |

TABLE 2-continued

| Gene name | A. Longa pomer Run #1 | A. Longa pomer Run #2 | Vehicle1 (phosphate buffer at pH 7.4) | Vehicle2 (phosphate buffer at pH 7.4) |
|---|---|---|---|---|
| PUC18 | 482.3333 | 213.7778 | 0.44 | 0.44 |
| Blank | 371.7778 | 213.7778 | 0.58 | 0.58 |
| Blank | 674.1111 | 371.3333 | 0.55 | 0.55 |
| AS1R2 | 371.3333 | 106.8889 | 0.29 | 0.29 |
| AS1R1 | 839.2778 | 53.44444 | 0.06 | 0.06 |
| AS1 | 639.1111 | 213.8333 | 0.33 | 0.33 |
| GAPD | 65535 | 65535 | 1 | 1 |
| B2M | 65535 | 65535 | 1 | 1 |
| HSPCB | 65535 | 65535 | 1 | 1 |
| HSPCB | 65535 | 65535 | 1 | 1 |
| ACTB | 65535 | 64985.22 | 0.99 | 0.99 |
| ACTB | 65535 | 58292.31 | 0.89 | 0.89 |
| BAS2C | 61685.06 | 35836.83 | 0.58 | 0.58 |
| BAS2C | 65535 | 65535 | 1 | 1 |

Example 4

Cellular Activity of *A. paucinervis* Pomel Extract in Killer T Cells

NK cells are a subset of lymphocytes that comprise about 10% of total lymphoid cells and have robust anti-tumor and anti-viral activities. Under physiological conditions, resting NK cells are implicated in immune surveillance where they recognize and destroy abnormal cell growth. Tumors usually develop after escaping the detection by these cells. Activated NK cells have been generated in vitro, and these cells have been used for the treatment of cancer patients with some success. The molecules that are used to generate activated NK cells are IL-2 or IL-15 (in certain cases IL-2-activated NK cells are also called LAK cells).

Figure 4:
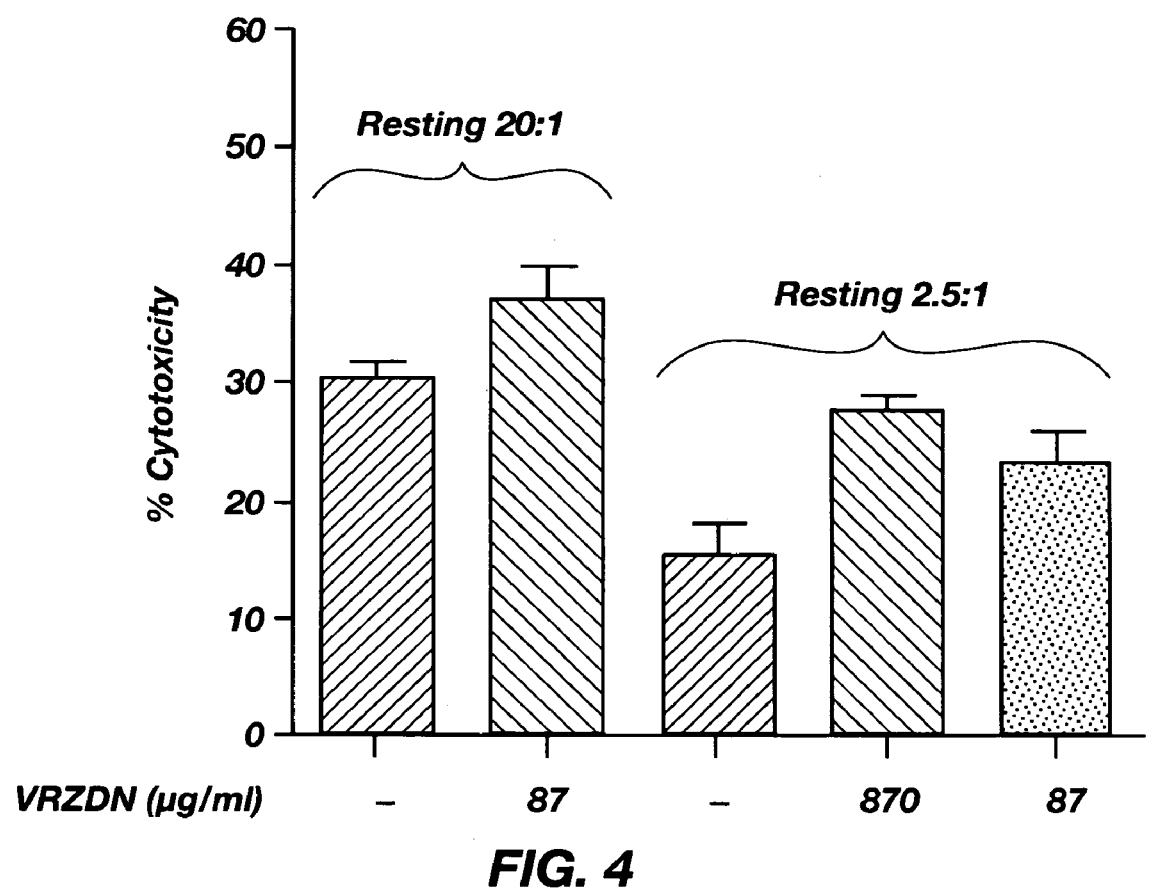
FIG. 4 shows the effects of an *A. paucinervis* pomel extract (VRZDN) on resting killer T cells.

Experiments were performed to determine the affect of *A. paucinervis* pomel extract on the killing function of resting NK cells. Results show that *A. paucinervis* pomel extract, particularly the dose of 87 μg/ml, increased the cytolytic activity of resting NK cells against the tumor target cells, K562. This dose of *A. paucinervis* pomel extract enhanced NK cell lysis when NK cells were used at 20:1 and 2.5:1 effector:target cell ratios. In addition, the same dose enhanced activated NK cell activity against K562. FIG. 4 shows the effect of different concentrations of *A. paucinervis* pomel extract on NK cell lysis at one effector:target cell ratio (1.25:1).

For these experiments NK cells were prepared as follows: Buffy coats were obtained from the San Diego blood bank. The cells were centrifuged on Histopaque gradient (Sigma Chemicals), and lymphocytes were collected. These cells were then incubated on nylon-wool columns (NWC) for one hour to remove B cells and monocytes. The cells that did not adhere to the NWC were collected, washed three times, and then incubated with target cells. In other cultures, $1 \times 10^6$/ml cells were incubated with 100 international units (IU) IL-2 for 24 hours. The plastic flasks non-adherent cells were removed, and the conditioned media was added back to the adherent cells. The cells were cultured for an additional seven days. At the end of the culture period, the cells were removed from plastic flasks using cell scrapers, washed extensively, and then incubated with target cells at various effector:target cell ratios.

Target cells utilized in this assay were the NK-sensitive K562, a myelogenous leukemia cell line. K562 cells were labeled with 5 μg/ml Calcien AM (TefLabs, Inc., Austin, Tex.) for 45 minutes. The cells were pelleted by centrifugation and resuspended in a RPMI. To obtain total cell lysis, these cells were incubated with Triton-X, whereas they were incubated with medium alone to obtain total viability. In other cultures, Calcien AM-labeled K562 were incubated with activated NK cells at different NK:K562 ratios (designated as effector:target or E:T cell ratio). Thus, 100000 activated NK cells incubated with 10000 K562 (10:1 E:T cell ratio), 50000 activated NK cells incubated with 10000 K562 (5:1 E:T ratio), 25000 activated NK cells incubated with 10000 K562 (2.5:1 E:T ratio), or 12500 activated NK cells incubated with 10000 K562 (1.25:1 E:T ratio).

The percentage of cytotoxicity was calculated according to the following formula: Percent viability=O.D. of K562 incubated with NK cells (experimental) minus O.D. of K562 incubated with Triton-X (total lysis), divided by O.D. of K562 incubated in media only (total viability) minus O.D. of K562 incubated with Triton X (total lysis). Percent cytotoxicity was then calculated as 100 minus percent viability. Percent cytotoxicity is the measurement of the level of NK cell lysis of target cells.

*A. paucinervis* pomel extract enhances the killing function of resting NK cells.

Example 5

Cellular Activity of *A. paucinervis* Pomel Extract in Human Blood

The hemolytic activity of *A. paucinervis* pomel extract on blood cells was examined, and compared with the ability of Triton-X to lyse these cells. *A. paucinervis* pomel extract at all dilutions examined did not have adverse effects on blood cells after a 0- to 14-day incubation. In contrast, almost all Triton-X concentrations (0.05-0.0025 dilutions) were toxic to blood cells post-incubation.

Figure 5A:
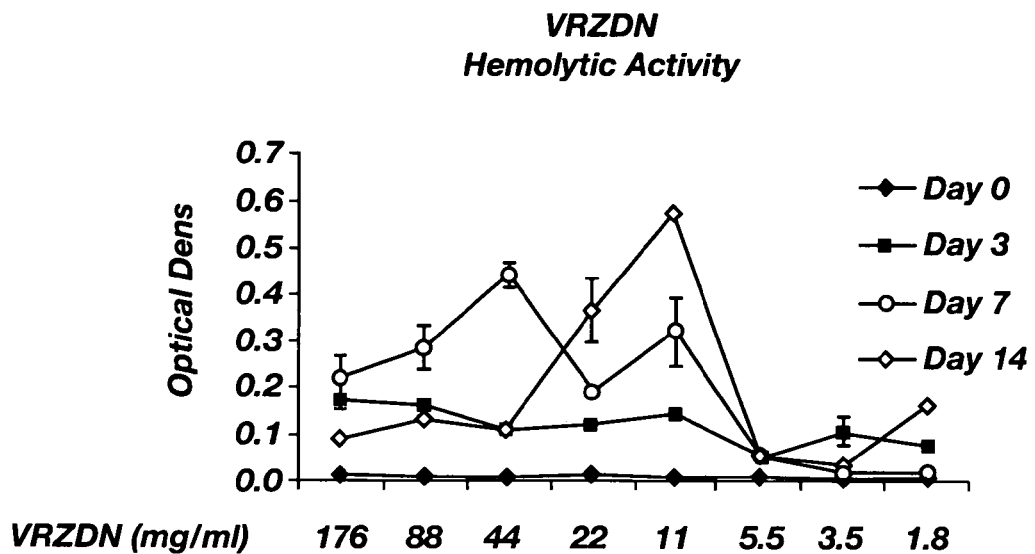
FIGS. 5A and 5B show the in vitro effect of various concentrations of *A. paucinervis* pomel extract (VRZDN) on the hemolysis of human red blood cells after incubation between 0 and 14 days and the in vitro effect of Triton-X on the same cells for the same time points.
Figure 5B:
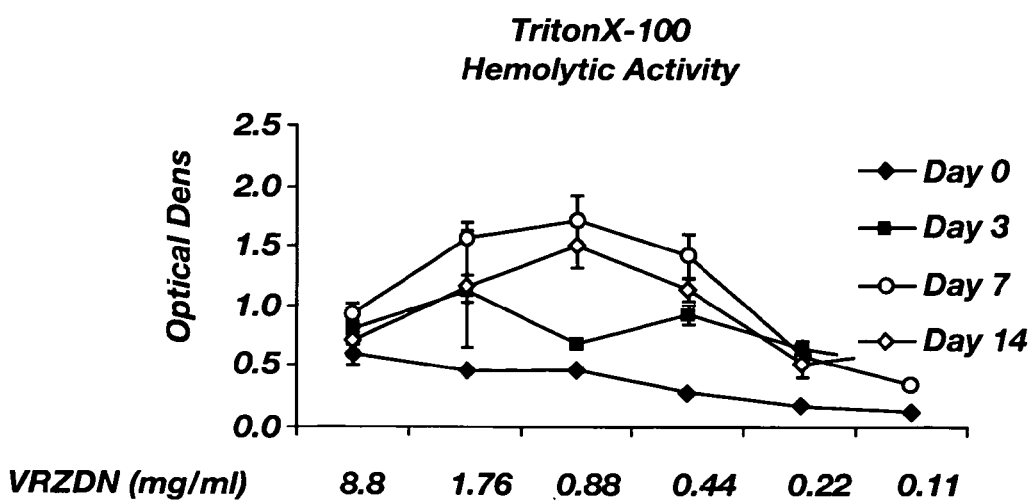

To perform these studies, heparinized-whole blood was incubated with dilutions of Triton-X-100 (0-1%) or 5× (4.4 mg/ml) *A. paucinervis* pomel extract for 40 minutes at room temperature. Plasma was collected after centrifugation at 1200×g for 5 minutes and diluted 1/20 with DPBS. The absorbance at 560 nm of 100 μl of each diluted plasma sample was measured. In a second experiment, the effects of incubating whole blood with dilutions of 5× (4.4 mg/ml) *A. paucinervis* pomel extract for 0, 3, 7 and 14 days was assessed. Experimental results are shown in FIG. 5A (cells treated with *A. paucinervis* pomel extract) and FIG. 5B (cells treated with Triton-X-100).

*A. paucinervis* pomel extract does not induce lysis of human blood cells in vitro.

Example 6

Cellular Activity of *A. paucinervis* Pomel Extract on Isolated Human Cells and Cultured Human Cells Experiments were performed to determine the effect of *A. paucinervis* pomel extract on polymorphonuclear cells (PMN) and HUVEC cells. For this study, cells were plated at a density of 50,000 cells/well in 200 μl and allowed to recover for two hours prior to the addition of extract.

Figure 11A:
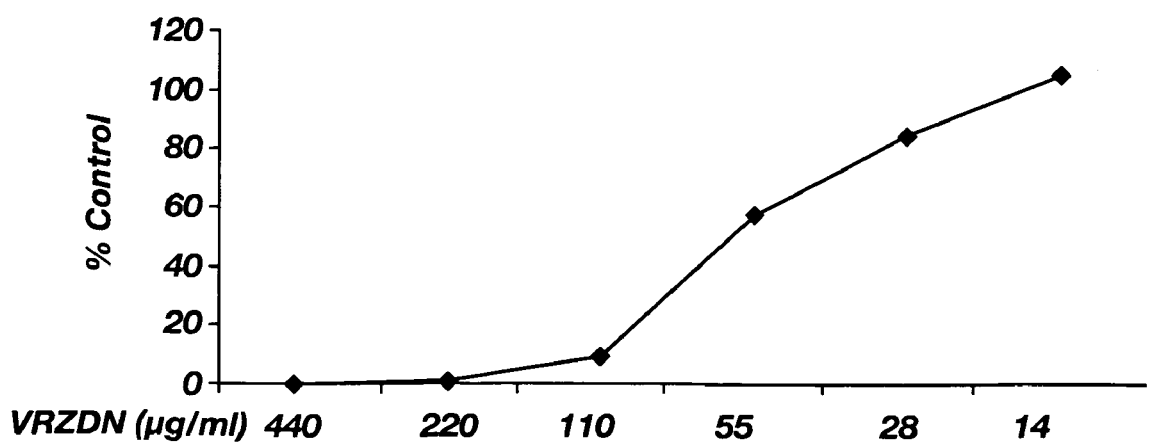
FIGS. 11A, 11B, and 11C show the effect of various concentrations of *A. paucinervis* pomel extract (VRZDN) on the survival and proliferation of polymorphonuclear cells (FIG. 11A); and PBMC and PMN cells (FIG. 11B); and HUVEC cells (FIG. 11C) after two and five days incubation.
Figure 11B:
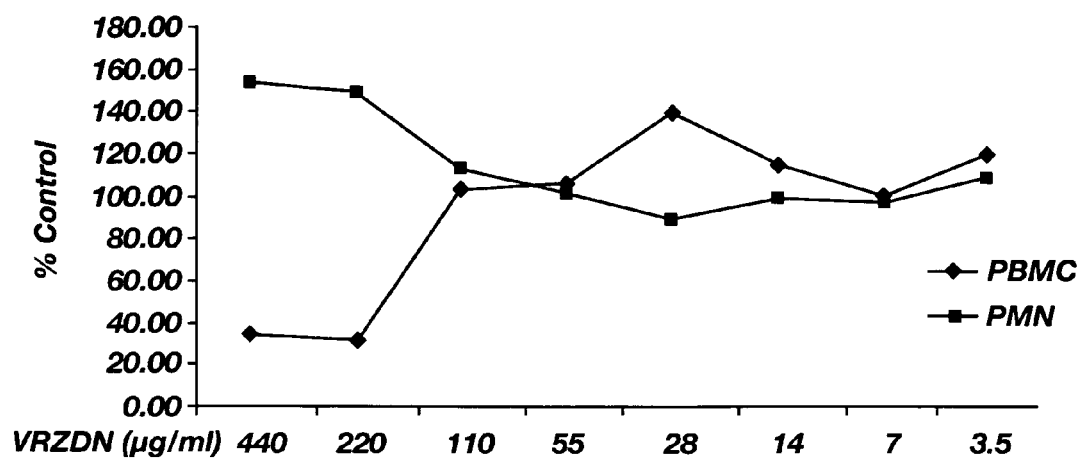
Figure 11C:
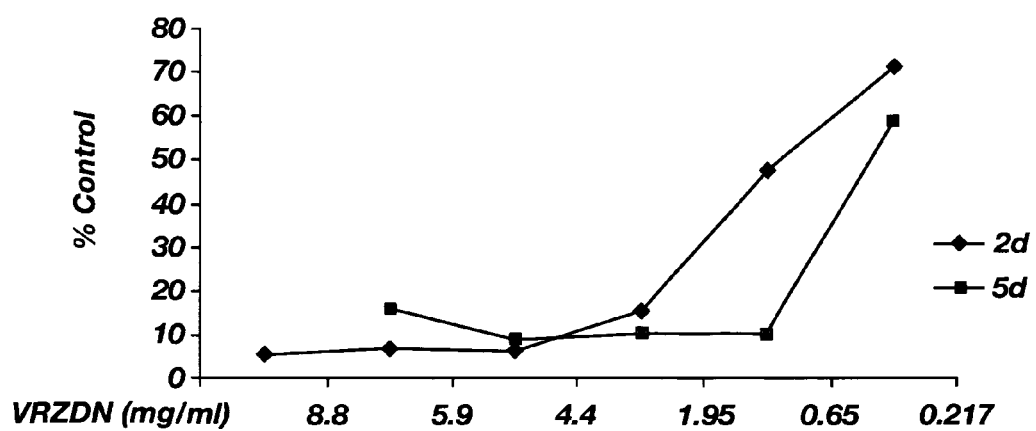

*A. paucinervis* pomel extract was found to be stimulatory for the proliferation of PMN and peripheral blood mononuclear cell (PMNC) cells, when used at concentrations between 440 or 220 ug/ml (FIG. 11A). The extract also was observed to be stimulatory for peripheral blood mononuclear cell (PMNC) proliferation (FIG. 11B). The effect of various concentrations of *A. paucinervis* pomel extract (ranging between 8.8-0.217 mg/ml) on human umbilical vein endothelial cells (HUVECs) was also tested in this assay, and no significant adverse effects were observed after a two- or five-day incubation (FIG. 11 C).

*A. paucinervis* pomel extract does not adversely affect growth of isolated human blood cells and cultured endothelial cells

Example 7

In Vivo Toxicology of *A. paucinervis* Pomel Extract

Toxicology studies were performed to determine the effect of *A. paucinervis* pomel extract on CD1 mice. These animals are highly susceptible to toxic materials, and they normally succumb easily. Mice injected IV with several doses of *A. paucinervis* pomel extract did not show any adverse signs. The weights of these mice were within the normal range and were similar to the weights of mice receiving water only. None of these animals died before the termination of the assay.

Figure 7A:
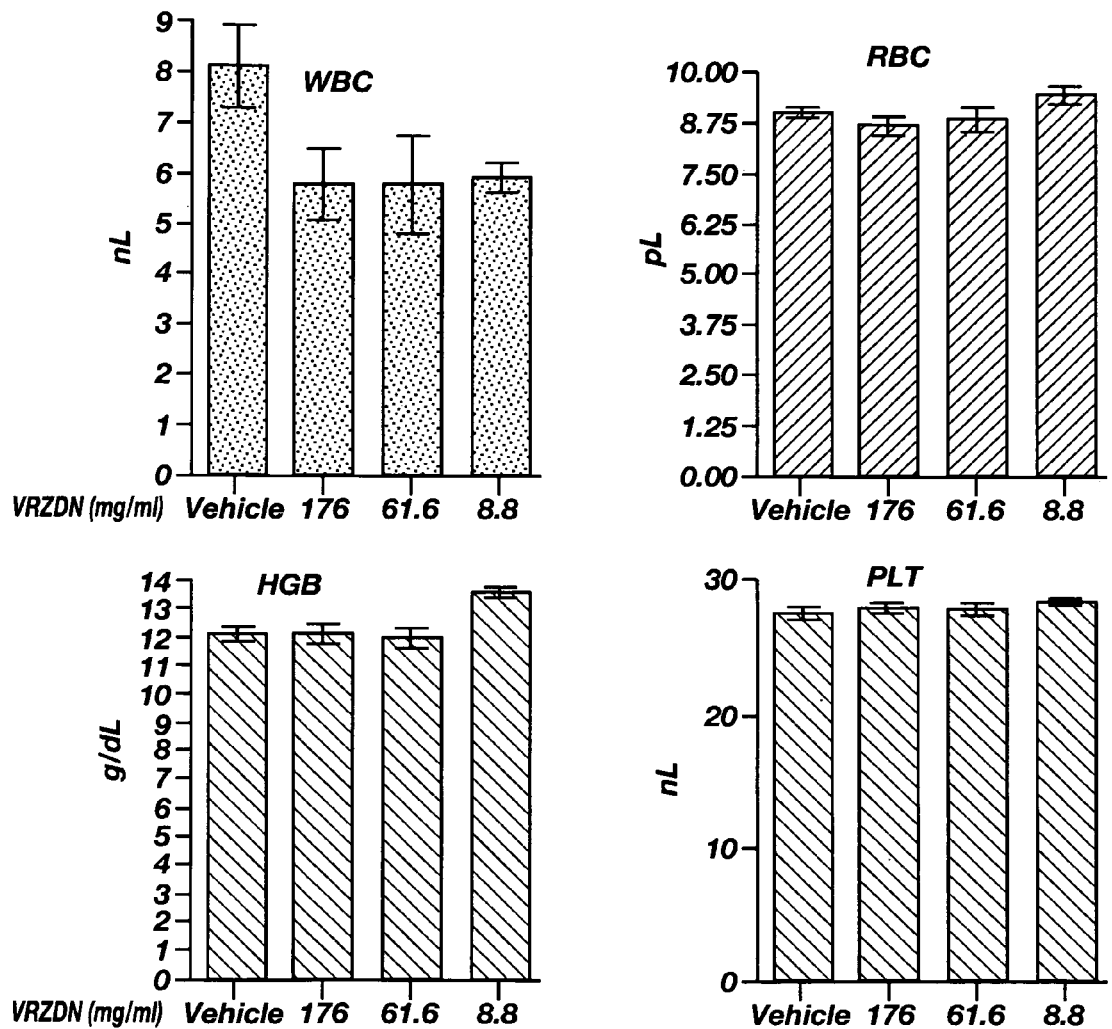
FIGS. 7A and 7B show the effect of IV administration of various concentrations of *A. paucinervis* pomel extract (VRZDN) on viability of white blood cells (WBC), red blood cells (RBC), Platelets (PLT) and hemoglobin (HGB) levels in CD1 mice and the effect of oral administration of various concentrations of *A. paucinervis* pomel extract on viability of white blood cells (WBC), red blood cells (RBC), Platelets (PLT) and hemoglobin (HGB) levels in CD1 mice, as compared to administration of water (Vehicle)

Mice were grouped into those receiving vehicle (receiving water; 5 mice), and those receiving 176.2 mg/ml (5 mice), 61.7 mg/ml (5 mice) or 8.81 mg/ml (5 mice). Intravenous administration of *A. paucinervis* pomel extract did not affect mouse white blood cell count, red blood cell count, platelet count or the level of hemoglobin. These levels were not significantly different from control untreated animals when examined between 1 and 14 days post-IV injection of the extract. FIG. 7A shows the effect of IV administration of various concentrations of *A. paucinervis* pomel extract on the viability of white blood cells (WBC), red blood cells (RBC), Platelets (PLT) or hemoglobulin levels in CD1 mice. *A. paucinervis* pomel extract was non-toxic to CD1 mice at intravenous dosages ranging from 8.81 mg/ml to 176.2 mg/ml.

Figure 7B:
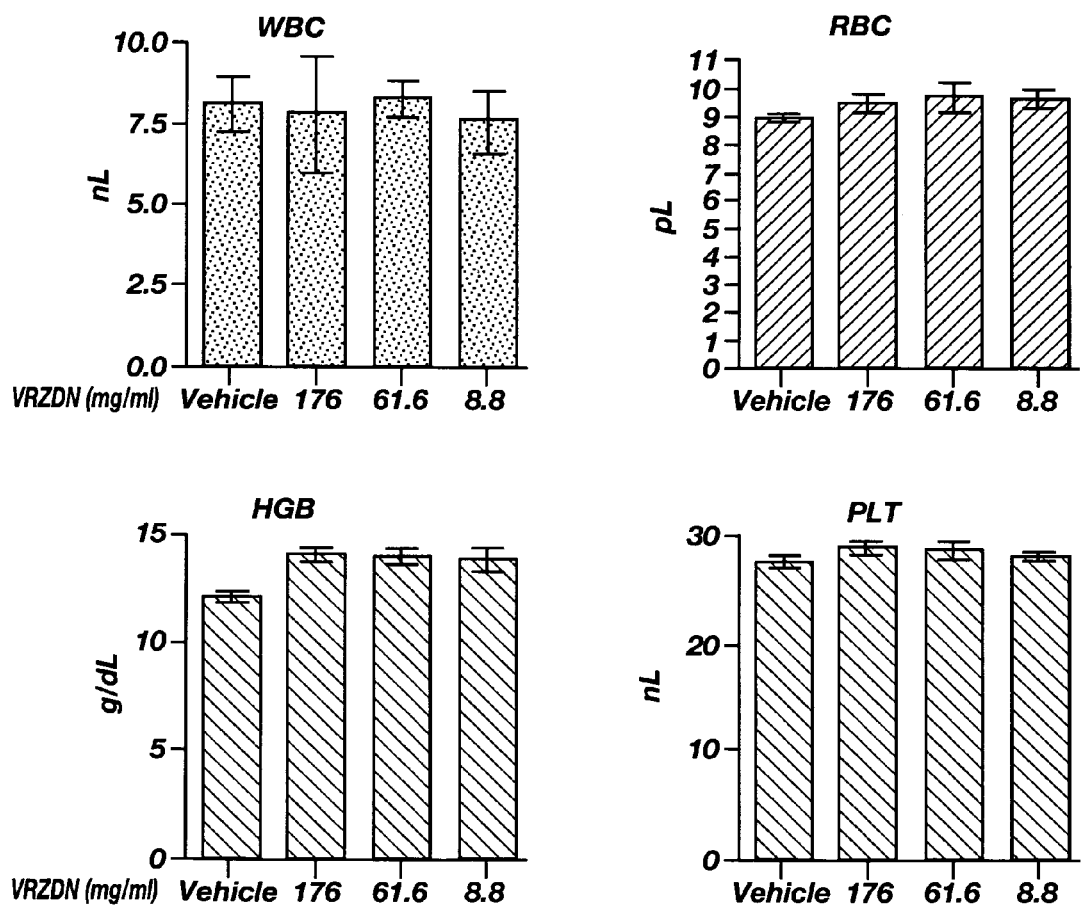

Toxicity in animals that received *A. paucinervis* pomel extract orally was also examined. Mice were either gavaged with vehicle (water; 5 mice), or with 176.2 mg/ml (5 mice), 61.7 mg/ml (5 mice), or 8.81 mg/ml (5 mice) of *A. paucinervis* pomel extract. Animals were examined between 1 and 28 days after the administration of the extract. The red blood cell counts, white blood cell counts, platelet counts and hemoglobin levels of treated animals were not significantly different from those of control animals (FIG. 7B).

Animals treated with *A. paucinervis* pomel extract by IV and oral delivery were found to have weights within the normal range and to be similar to the weights of mice receiving water only. No animals died before termination of this experiment. *A. paucinervis* pomel extract was non-toxic to CD1 mice at oral dosages ranging from 8.81 mg/ml to 176.2 mg/ml. *A. paucinervis* pomel extract was non-toxic to mice at various intravenous and oral dosages.

Example 8

Effects of *A. paucinervis* Pomel Extract on Organ Function

The effect of *A. paucinervis* pomel extract on liver function was determined by measuring the levels of the enzymes alanine aminotransferase (ALT; also known as glutamate pyruvate transaminase or SGPT) and aspartate aminotransferase (AST, also known as glutamic oxalacetic transaminase or SGOT). The levels of ALT and AST are elevated during pathological conditions including hepatitis, cirrhosis, myocardial infarction, and metastatic cancers, due to the injury of tissues such as the liver, heart, muscle and kidney. Thus, levels of ALT and AST in the liver of an animal provide a read-out of organ function at the time of testing.

Figure 8A:
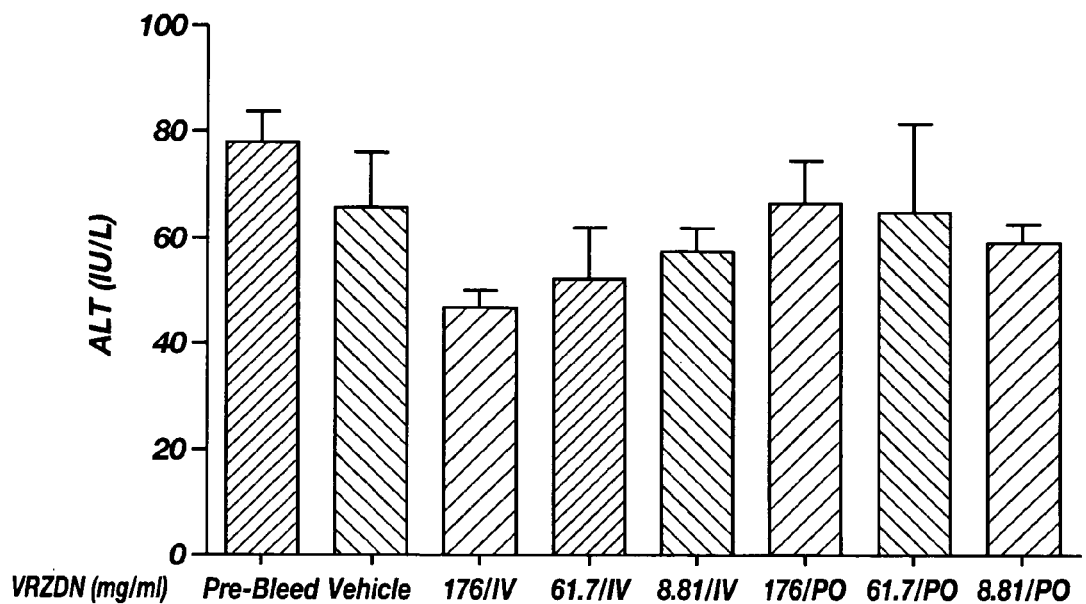
FIGS. 8A, 8B, and 8C show the effect of IV injecting or gavaging CD1 mice with various concentrations of *A. paucinervis* pomel extract (VRZDN) on the level of ALT (FIG. 8A); AST (FIG. 8B); and creatinine (FIG. 8C)
Figure 8B:
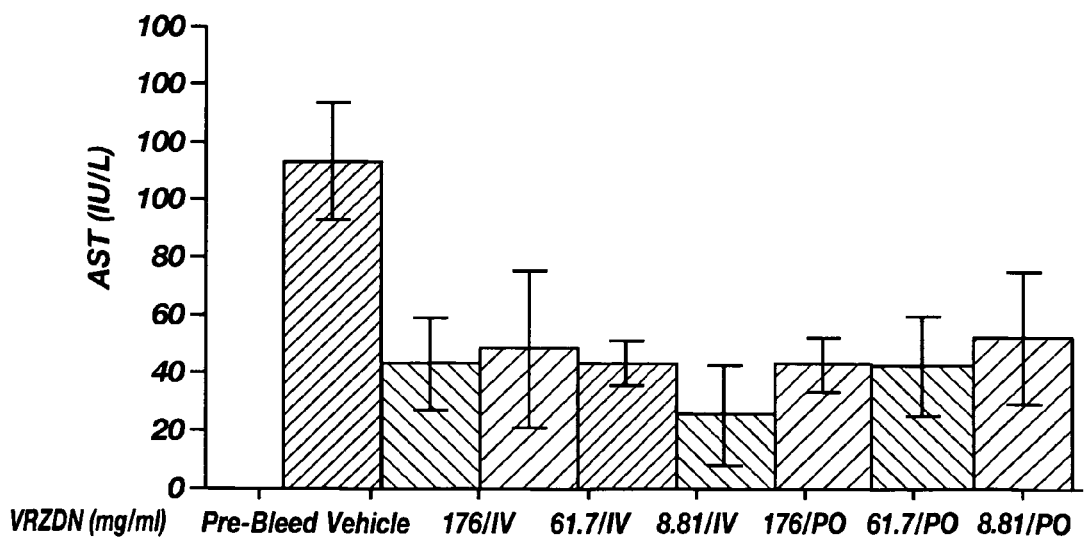

*A. paucinervis* pomel extract was administered to CD1 mice either by IV injection or gavage. Results in FIG. 8A show that the levels of ALT in the serum of CD1 receiving several doses of *A. paucinervis* pomel extract either IV or PO, were not significantly different from those mice administered with vehicle. Similarly, no effect was observed on the level of AST from sera of CD 1 mice treated with either vehicle or with various concentrations of *A. paucinervis* pomel extract either IV or PO (FIG. 8B). Collectively, these results indicate that *A. paucinervis* pomel extract is nontoxic to the function of the liver.

Figure 8C:
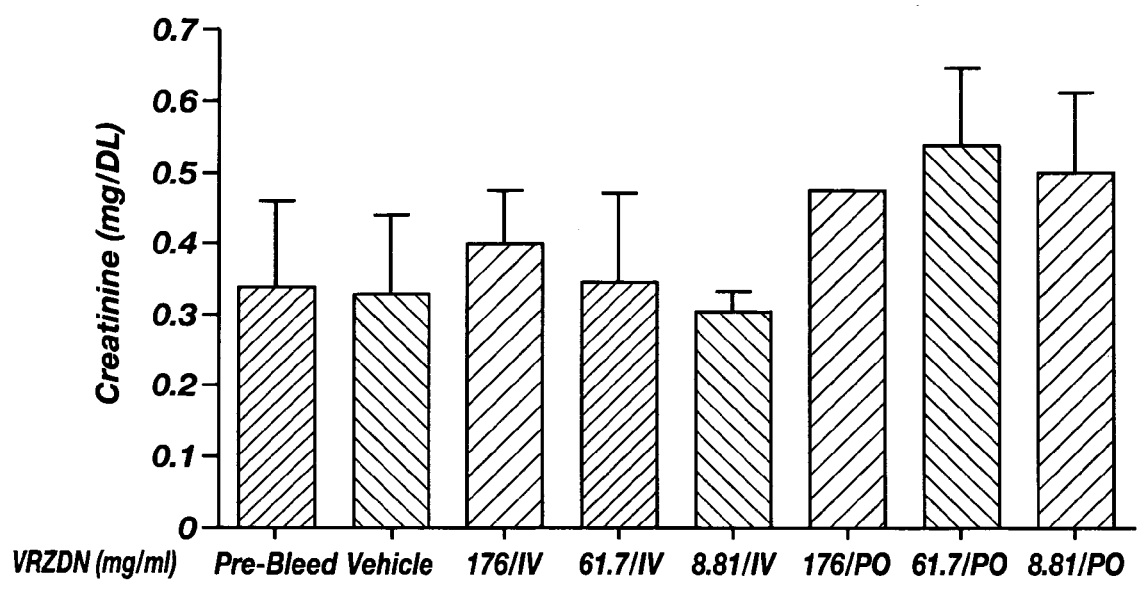

The effect of *A. paucinervis* pomel extract on kidney function in CD1 mice was examined. Creatinine is generated upon spontaneous dehydration of the kidneys. It is secreted by the kidneys, and its elevation is an indication of kidney damage and dysfunction. Sera of CD1 mice receiving various doses of *A. paucinervis* pomel extract either IV or PO were examined. Results in FIG. 8C demonstrate that the level of creatinine in the sera of mice treated with *A. paucinervis* pomel extract is not significantly different from mice receiving vehicle control. These results indicate that *A. paucinervis* pomel extract does not affect the function of the kidneys, and has no toxic effect on this organ.

Example 9

Effects of *A. paucinervis* Pomel Extract on Liver Function

Figure 9A:
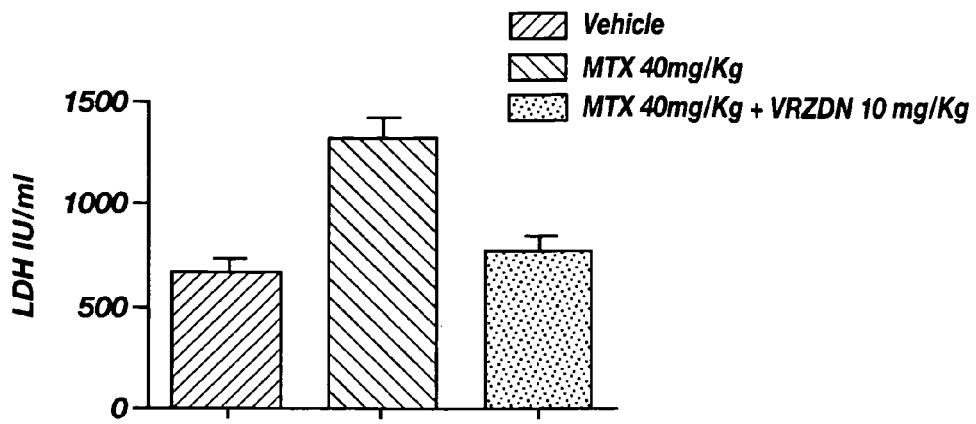
FIGS. 9A, 9B, and 9C show the effect of various concentrations of *A. paucinervis* pomel extract (VRZDN) on the level of LDH (FIG. 9A); billirubin (FIG. 9B) and AST (FIG. 9C) in Lewis rats undergoing methotraxate-induced liver damage.
Figure 9B:
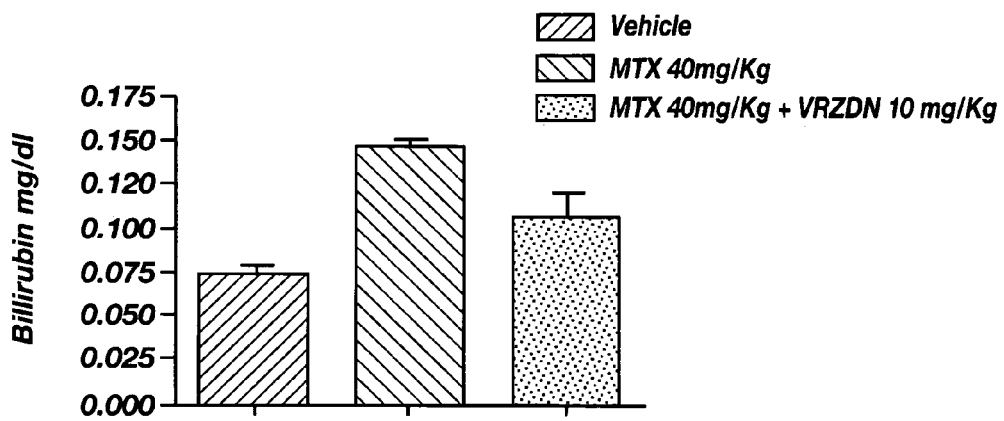
Figure 9C:
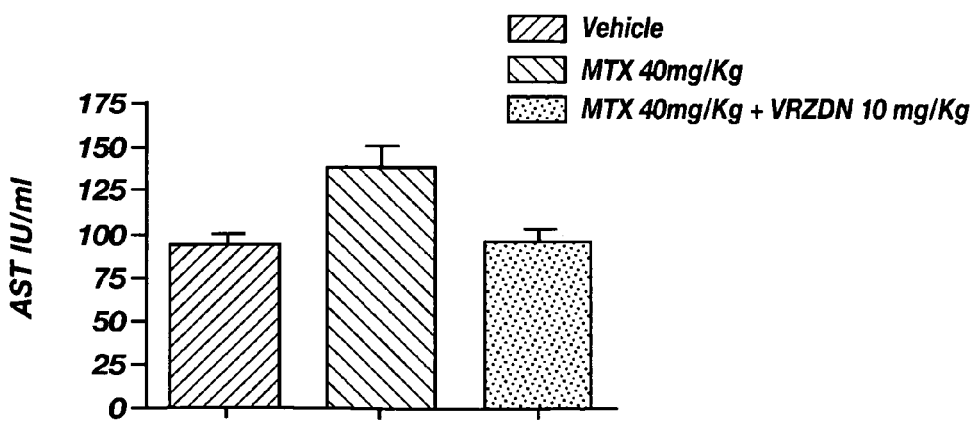

CD1 mice injected with high doses of *A. paucinervis* pomel extract repeated intravenously for 14 days or repeated b.i.d. orally for 28 consecutive days showed no signs of toxicity as determined by gross necropsy, clinical chemistry test of the liver, heart and kidney functions (ALT, AST, Creatinine). Furthermore, the levels of RBC, WBC, platelets and hemoglobin were within the normal range. *A. paucinervis* pomel extract protects Lewis rats from methotraxate-induced liver damage by normalizing the levels of liver function enzymes (AST, LDH, Billirubin). The results are depicted in FIGS. 9A-9C.

Example 10

In Vivo Effects of *A. paucinervis* Pomel Extract in Mice

Figure 10A:
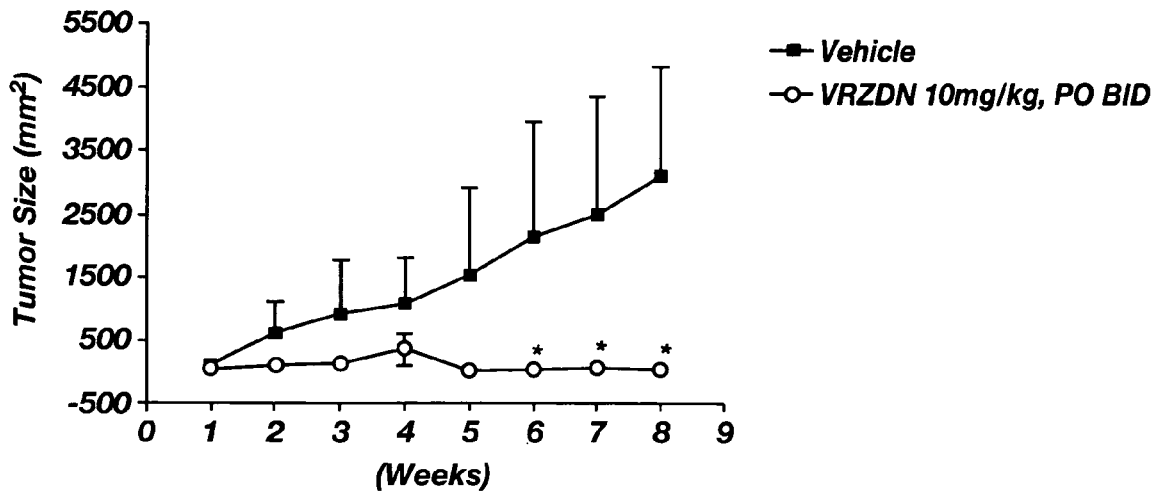
FIGS. 10A, 10B, and 10C show the effect of various concentrations of *A. paucinervis* pomel extract (VRZDN) on Colo-205 tumor growth in a mouse xenograft model (FIG. 10A); survival of mice transplanted intracranially with U87MG glioblastoma cells (FIG. 10B); and A431 carcinoma in a mouse xenograft model (FIG. 10C)

*A. paucinervis* pomel extract was administered to human xenograft bearing colo-205 tumor cells at a dosage of 10 mg/kg PO BID for eight weeks. As is shown in FIG. 10A, mice treated with *A. paucinervis* pomel extract had no detectable tumor growth, in comparison with mice treated with vehicle.

Figure 10B:
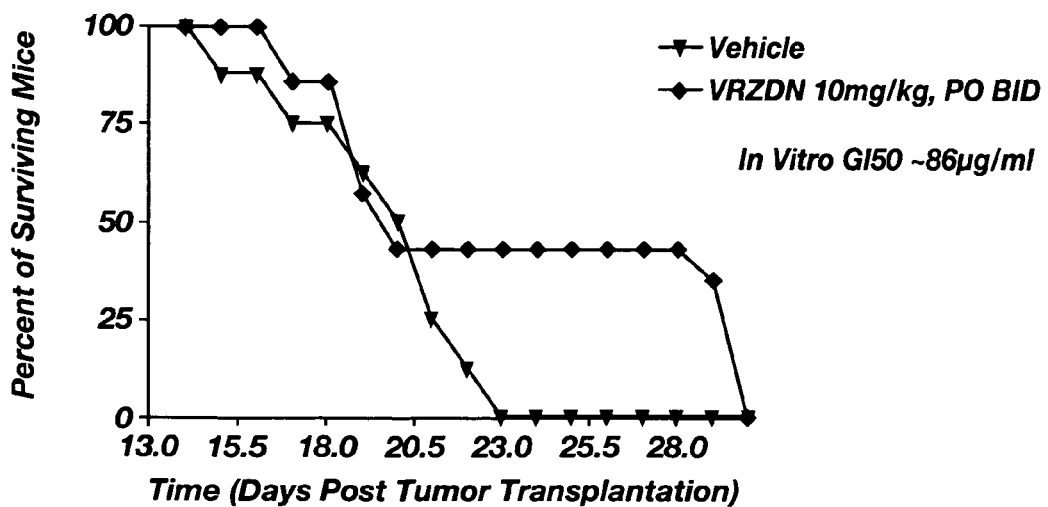

*A. paucinervis* pomel extract was administered to mice transplanted intracranially with U87MG glioblastoma cells at a dosage of 10 mg/kg PO BID for 30 days. As is shown in FIG. 10B, mice treated with *A. paucinervis* pomel extract had significantly improved survival rates in comparison with mice treated with vehicle.

Figure 10C:
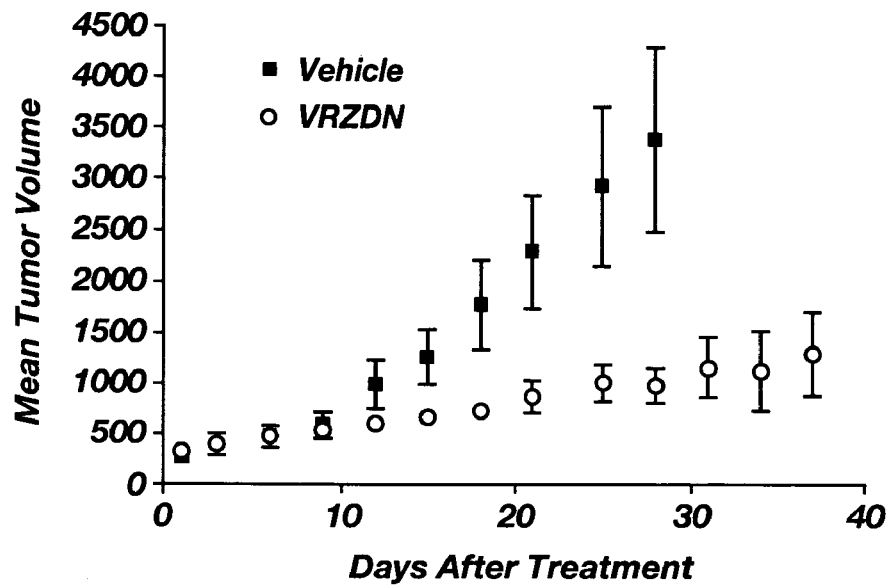

*A. paucinervis* pomel extract was administered to human xenograft mice bearing A431 human epithelia carcinoma cells at a dosage of 10 mg/kg PO BID for 38 days. As is shown in FIG. 10C, mice treated with *A. paucinervis* pomel extract had significantly reduced tumor volume, in comparison with mice treated with vehicle.

Experiments were performed essentially as follows: each mouse was inoculated subcutaneously with an inoculum of $1.5 \times 10^6$ cells in a 1:1 ratio with matrigel using a 21 G needle and syringe. Tumor volumes were monitored and calculated using the formula: Tumor volume=(a2×b/2) where "a" is the smallest diameter and "b" is the largest diameter. Once the established tumors reach approximately 75-150 mm³ (individual tumor volumes may range from 100 to 250 mg) the mice were assigned into the various vehicle control and treatment groups such that the mean tumor volumes in the treated groups were within 10% of the mean tumor weight in the vehicle control group. On the same day, drug injections were administered according to the drug schedule.

*A. paucinervis* pomel extract reduced tumor cell growth in three mouse models.

Example 11

Applications

Extracts of the plant *A. paucinervis* pomel are both non-toxic and effective for treating cancer in humans. The case studies described in the following Examples did not involve identifying subjects having liver sensitivity.

Case studies to examine efficacy and possible toxic side-effects of *A. paucinervis* pomel extract are performed. In one case, a 34-year-old married woman with one child has breast cancer. She receives mammectomy and chemotherapy. At the same time she receives *A. paucinervis* pomel extract for two years with no side effects. Five years later, she remains free of cancer.

Example 12

A 61-year-old woman has breast cancer for twenty years. She receives *A. paucinervis* pomel extract for three years with no side effects. She remains free of cancer.

Example 13

A woman has colon cancer and is treated using surgery, radiotherapy and chemotherapy. She receives *A. paucinervis* pomel extract at the time of treatment and continues to receive *A. paucinervis* pomel extract with no side effects or cancer recurrence for several years.

Example 14

A 43-year-old woman has breast cancer, and is treated using mammectomy and chemotherapy. She receives *A. paucinervis* pomel extract at the time of treatment and continues to receive *A. paucinervis* pomel extract with no side effects or cancer recurrence for several years.

Example 15

A 67-year-old male has pancreatic cancer. Although he receives chemotherapy and radiotherapy, six months later his therapy is discontinued because metastases are detected. He is provided with *A. paucinervis* pomel extract for three years. This patient is examined later, and has normal renal hepatic and pulmonary test results. His tumor is reduced in mass.

Example 16

A 58-year-old patient's history, hospitalized for icterus resulting from alcoholic hepatitis, is followed. This patient receives one-half teaspoon of *A. paucinervis* pomel extract for 40 days, stops taking the extract for 10 days, and then resumes taking the extract for an additional 40 days. This patient reports no side effects of any sort three years following this regiment. His transaminase level is normal, and no nephrotoxicity is observed in this patient.

While this invention has been described in certain embodiments, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of making a concentrated biologically active extract of *Aristolochia paucinervis* pomel, the method comprising:
   extracting an un-extracted powder of the root and/or bark of *Aristolochia paucinervis* pomel with water to form a biologically active extract; and
   contacting an un-extracted powder of the root and/or bark of *Aristolochia paucinervis* pomel with the biologically active extract to from a concentrated biologically active extract.

2. The method of claim 1, wherein the extracting is performed at a temperature between about 20° C. and about 40° C.

3. The method of claim 1, wherein the concentrated biologically active extract contains at least 10 wt. % dissolved biological materials from *Aristolochia paucinervis* pomel.

4. The method of claim 1, wherein the concentrated biologically active extract contains at least 20 wt. % dissolved biological materials from *Aristolochia paucinervis* pomel.

5. The method of claim 1, wherein contacting un-extracted powder of the root and/or bark of *Aristolochia paucinervis* pomel with the biologically active extract to form a concentrated biologically active extract of *Aristolochia paucinervis* pomel is repeated at least five times.

6. The method of claim 1, wherein contacting un-extracted powder of the root and/or bark of *Aristolochia paucinervis* pomel with the biologically active extract to form a concentrated biologically active extract of *Aristolochia paucinervis* pomel is repeated at least 100 times.

7. The method of claim 1, further recovering the solutes in the extract.

* * * * *

UNITED STATES PATENT AND TRADEMARK OFFICE
CERTIFICATE OF CORRECTION

PATENT NO. : 8,003,137 B2
APPLICATION NO. : 12/151843
DATED : August 23, 2011
INVENTOR(S) : Bassam Damaj It is certified that error appears in the above-identified patent and that said Letters Patent is hereby corrected as shown below:

In the specification:

| | | |
|---|---|---|
| COLUMN 21, | LINES 32,33, | Change both instances of "*Longa pomer*" to --*paucinervis pomel*-- |
| COLUMN 22, | LINES 3,4, | Change both instances of "*Longa pomer*" to --*paucinervis pomel*-- |
| COLUMN 22, | LINE 50, | Change "SERPINE1" to --SERPIN1-- |
| COLUMN 23, | LINES 3,4, | Change both instances of "*Longa pomer*" to --*paucinervis pomel*-- |

In the claims:

CLAIM 1, COLUMN 28, LINE 34, Change "from" to --form--

Signed and Sealed this
Twenty-third Day of April, 2013

Teresa Stanek Rea
*Acting Director of the United States Patent and Trademark Office*